(12) United States Patent
Gysling et al.

(10) Patent No.: US 7,380,438 B2
(45) Date of Patent: Jun. 3, 2008

(54) APPARATUS AND METHOD FOR PROVIDING A FLUID CUT MEASUREMENT OF A MULTI-LIQUID MIXTURE COMPENSATED FOR ENTRAINED GAS

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 11/227,713

(22) Filed: Sep. 15, 2005

(65) Prior Publication Data

US 2006/0053869 A1 Mar. 16, 2006

Related U.S. Application Data

(60) Provisional application No. 60/654,355, filed on Feb. 18, 2005, provisional application No. 60/610,450, filed on Sep. 16, 2004.

(51) Int. Cl.
*G01N 9/24* (2006.01)
*G01N 9/26* (2006.01)
*G01N 33/18* (2006.01)

(52) U.S. Cl. ............... 73/19.1; 73/19.05; 73/19.11; 702/24; 702/25

(58) Field of Classification Search ............... 73/19.01, 73/19.03, 19.04, 19.08, 19.1, 19.11; 324/637, 324/639, 640, 647, 654, 655, 656; 702/24, 702/25

See application file for complete search history.

(56) References Cited

U.S. PATENT DOCUMENTS 2,874,568 A 2/1959 Petermann (Continued)

FOREIGN PATENT DOCUMENTS

EP 222503 5/1987

(Continued)

OTHER PUBLICATIONS

Nyfors Ebbe et al: Mixtures of Oil, Water, and Gas with Microwave Sensors. New Developments and Field Experience of the MFI MultiPhase, and WaterCut Meters of Roxar, Proc SPIE Int Soc Opt Eng: Proceedings of SPIE—The International Society for Optical Engineering 200 Society of Photo-Optical Instrumentation Engineers, Bellinghma, WA, USA, vol. 4129, 2000, pp. 12-21, XP002402006—Paragraphs [02.4], [04.1].

(Continued)

*Primary Examiner*—Hezron Williams
*Assistant Examiner*—David A. Rogers

(57) ABSTRACT

An apparatus for determining a fluid cut measurement of a multi-liquid mixture includes a first device configured to sense at least one parameter of the mixture to determine a fluid cut of a liquid in the mixture. A second device is configured to determine a concentration of gas in the mixture in response to a speed of sound in the mixture; and a signal processor is configured to adjust the fluid cut of the liquid using the concentration of the gas to determine a compensated fluid cut of the liquid. The parameter of the mixture sensed by the first device may include a density of the mixture (e.g., by way of a Coriolis meter), a permittivity of the mixture (e.g., by way of a resonant microwave oscillator), or an amount of microwave energy absorbed by the mixture (e.g., by way of a microwave absorption watercut meter). The signal processor may employ different correction factors depending on the type of fluid cut device used. The second device may include a gas volume fraction meter.

36 Claims, 14 Drawing Sheets

U.S. PATENT DOCUMENTS

| | | | |
|---|---|---|---|
| 3,444,723 A | 5/1969 | Wakefield | |
| 3,780,577 A | 12/1973 | Brown | |
| 4,004,461 A | 1/1977 | Lynworth | |
| 4,048,853 A | 9/1977 | Smith et al. | |
| 4,080,837 A | 3/1978 | Alexander et al. | |
| 4,144,754 A | 3/1979 | Pitts et al. | |
| 4,195,517 A | 4/1980 | Kalinoski et al. | |
| 4,248,085 A | 2/1981 | Coulthard | |
| 4,262,523 A | 4/1981 | Stansfeld | |
| 4,445,389 A | 5/1984 | Potzick et al. | |
| 4,580,444 A | 4/1986 | Abts et al. | |
| 4,773,257 A | 9/1988 | Aslesen et al. | |
| 4,823,613 A | 4/1989 | Cage et al. | |
| 4,862,060 A * | 8/1989 | Scott et al. | 324/639 |
| 4,896,540 A | 1/1990 | Shakkottai et al. | |
| 4,902,961 A * | 2/1990 | De et al. | 324/640 |
| 5,029,482 A | 7/1991 | Liu et al. | |
| 5,040,415 A | 8/1991 | Barkhoudarian | |
| 5,049,823 A * | 9/1991 | Castel et al. | 324/640 |
| 5,083,452 A | 1/1992 | Hope | |
| 5,101,163 A * | 3/1992 | Agar | 324/639 |
| 5,218,197 A | 6/1993 | Carroll | |
| 5,224,372 A | 7/1993 | Kolpak et al. | |
| 5,259,239 A | 11/1993 | Gaisford | |
| 5,285,675 A | 2/1994 | Colgate et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,526,844 A | 6/1996 | Kamen et al. | |
| 5,591,922 A | 1/1997 | Segeral et al. | |
| 5,594,180 A | 1/1997 | Carpenter et al. | |
| 5,654,502 A | 8/1997 | Dutton | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,845,033 A | 12/1998 | Berthold et al. | |
| 5,856,622 A | 1/1999 | Yamamoto et al. | |
| 5,948,959 A | 9/1999 | Peloquin | |
| 6,016,702 A | 1/2000 | Maron | |
| 6,065,328 A | 5/2000 | Dayton et al. | |
| 6,151,958 A | 11/2000 | Letton et al. | |
| 6,202,494 B1 | 3/2001 | Ricbel et al. | |
| 6,209,388 B1 | 4/2001 | Letton et al. | |
| 6,318,156 B1 | 11/2001 | Dutton | |
| 6,335,959 B1 | 1/2002 | Lynch et al. | |
| 6,354,147 B1 | 3/2002 | Gysling et al. | |
| 6,378,357 B1 | 4/2002 | Han et al. | |
| 6,397,683 B1 | 6/2002 | Hagenmeyer et al. | |
| 6,401,538 B1 | 6/2002 | Han et al. | |
| 6,422,092 B1 | 7/2002 | Morrison et al. | |
| 6,442,092 B1 | 7/2002 | Morrison et al. | |
| 6,435,030 B1 | 8/2002 | Gysling et al. | |
| 6,443,226 B1 | 9/2002 | Diener et al. | |
| 6,450,037 B1 | 9/2002 | Davis et al. | |
| 6,463,813 B1 | 10/2002 | Gysling | |
| 6,502,465 B1 | 1/2003 | Vedapuri et al. | |
| 6,502,466 B1 | 1/2003 | Cage et al. | |
| 6,532,827 B1 | 3/2003 | Ohnishi | |
| 6,536,291 B1 | 3/2003 | Gysling et al. | |
| 6,550,342 B2 | 4/2003 | Croteau et al. | |
| 6,558,036 B2 | 5/2003 | Gysling et al. | |
| 6,575,043 B1 | 6/2003 | Huang et al. | |
| 6,587,798 B2 | 7/2003 | Gysling et al. | |
| 6,601,458 B1 | 8/2003 | Gysling et al. | |
| 6,609,069 B2 | 8/2003 | Gysling | |
| 6,672,163 B2 | 1/2004 | Han et al. | |
| 6,691,584 B2 | 2/2004 | Gysling et al. | |
| 6,698,297 B2 | 3/2004 | Gysling | |
| 6,732,575 B2 | 5/2004 | Gysling et al. | |
| 6,745,135 B2 | 6/2004 | Keilty et al. | |
| 6,763,698 B2 | 7/2004 | Greenwood | |
| 6,776,054 B1 | 8/2004 | Stephenson et al. | |
| 6,782,150 B2 | 8/2004 | Davis et al. | |
| 6,802,224 B2 | 10/2004 | Nakao et al. | |
| 6,813,962 B2 | 11/2004 | Gysling et al. | |
| 6,817,229 B2 | 11/2004 | Han et al. | |
| 6,837,098 B2 | 1/2005 | Gysling et al. | |
| 6,862,920 B2 | 3/2005 | Gysling et al. | |
| 6,868,737 B2 | 3/2005 | Croteau et al. | |
| 6,889,562 B2 | 5/2005 | Gysling et al. | |
| 6,898,541 B2 | 5/2005 | Gysling et al. | |
| 6,945,095 B2 | 9/2005 | Johansen | |
| 6,950,760 B2 | 9/2005 | Henry et al. | |
| 6,959,604 B2 | 11/2005 | Davis et al. | |
| 6,971,259 B2 | 12/2005 | Gysling | |
| 6,988,411 B2 | 1/2006 | Gysling | |
| 7,059,199 B2 | 6/2006 | Mattar et al. | |
| 7,086,278 B2 | 8/2006 | Gysling et al. | |
| 7,134,320 B2 | 11/2006 | Banach et al. | |
| 2001/0045134 A1 | 11/2001 | Henry et al. | |
| 2002/0095263 A1 | 7/2002 | Gysling | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0016284 A1 | 1/2004 | Gysling et al. | |
| 2004/0069069 A1 | 4/2004 | Croteau | |
| 2004/0074312 A1 | 4/2004 | Gysling | |
| 2004/0139791 A1 | 7/2004 | Johansen | |
| 2004/0144182 A1 | 7/2004 | Gysling | |
| 2004/0167735 A1 | 8/2004 | Gysling et al. | |
| 2004/0168522 A1 | 9/2004 | Fernald et al. | |
| 2004/0194539 A1 | 10/2004 | Gysling | |
| 2004/0199340 A1 | 10/2004 | Gysling et al. | |
| 2004/0199341 A1 | 10/2004 | Gysling et al. | |
| 2004/0210404 A1 | 10/2004 | Gysling et al. | |
| 2004/0216509 A1 | 11/2004 | Antonijevic | |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |
| 2005/0005711 A1 | 1/2005 | Gysling et al. | |
| 2005/0005712 A1 | 1/2005 | Gysling et al. | |
| 2005/0005713 A1 | 1/2005 | Winston et al. | |
| 2005/0011258 A1 | 1/2005 | Gysling et al. | |
| 2005/0011283 A1 | 1/2005 | Gysling et al. | |
| 2005/0011284 A1 | 1/2005 | Gysling et al. | |
| 2005/0012935 A1 | 1/2005 | Kersey | |
| 2005/0033545 A1 | 2/2005 | Gysling et al. | |
| 2005/0039520 A1 | 2/2005 | Bailey et al. | |
| 2005/0044929 A1 | 3/2005 | Gysling et al. | |
| 2005/0044966 A1 | 3/2005 | Croteau et al. | |
| 2005/0050956 A1 | 3/2005 | Croteau et al. | |
| 2005/0061060 A1 | 3/2005 | Banach et al. | |
| 2005/0072216 A1 | 4/2005 | Engel | |
| 2005/0120799 A1 | 6/2005 | Gysling et al. | |
| 2005/0138993 A1 | 6/2005 | Mattar et al. | |
| 2005/0171710 A1 | 8/2005 | Gysling et al. | |
| 2005/0188771 A1 | 9/2005 | Lund Bo et al. | |
| 2005/0193832 A1 | 9/2005 | Tombs et al. | |
| 2005/0210965 A1 | 9/2005 | Sinha | |

FOREIGN PATENT DOCUMENTS

| | | |
|---|---|---|
| EP | 253504 | 1/1988 |
| GB | 2009931 | 6/1979 |
| GB | 2282931 | 4/1995 |
| WO | WO 93/14382 | 7/1993 |
| WO | WO 99/67629 | 12/1999 |

| WO | WO 2004/072588 | 8/2004 |

OTHER PUBLICATIONS

Mehdizadeh P: "Test Verifies Water-0Cut Meter Accuracy in SteamFlood" Oil and Gas Journal, Pennwell, Houston, TX, US, vol. 98, No. 40, Oct. 2, 2000—pp. 97-98, 100 XP000968244, issn: 0030-1388—Figure 2.

Whitaker T.S.: "Multiphase Flow Measurement: Current and Future Developments [for offshore industry use]" IEE Colloquium on Advances in Sensors for Fluid Flow Measurement, 1996, pp. 1-1, XP006510537.

"PVDF and Array Transducers" Author: Robert A. Day—NDTnet—Sep. 1996—vol. No. 9.

"Polymer Piezoelectric Transducers for Ultrasonic NDE" Aughors: Yoseph Bar-Cohen, Tianji Xue and Shyh-Shiuh Lih.

"Piezoelectric Polymers" ICASE Report No. 2001-43—Dec. 2001.

"Piezo Film Sensors Technical Manual" P/N 1005663-1 Rev. B Apr. 2, 1999.

U.S. Appl. No. 10/712,833.
U.S. Appl. No. 60/441,652.
U.S. Appl. No. 60/441,395.
U.S. Appl. No. 10/756,922.

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenutation of Acoustic Waves in Suspensions" by R.L. Gibson, Jr. and M.N. Toksoz.

Sonar-Based Volumetric Flow Meter For Pulp and Paper Applications—Daniel L. Gysling & Douglas H. Loose—Dec. 13, 2003.

Sonar-Based Volumetric Flow Meter for Chemical and Petrochemical Applications—Daniel L. Gysling & Douglas H. Loose—Feb. 14, 2003.

New Flowmeter Principle—By Walt Boyes—Flow Control Magazine—Oct. 2003 Issue.

SONAR Gets into the Flow—Daniel L. Gysling and Douglas H. Loose—Modern Process—Jan. 2004.

U.S. Appl. No. 60/445,795, filed Feb. 10, 2003.
U.S. Appl. No. 60/452,934, filed Mar. 10, 2003.
U.S. Appl. No. 60/549,161, filed Mar. 3, 2004.
U.S. Appl. No. 60/712,833.
U.S. Appl. No. 10/892,886.
U.S. Appl. No. 10/712,812.
U.S. Appl. No. 10/712,813.
U.S. Appl. No. 10/512,401.
U.S. Appl. No. 10/712,818.
U.S. Appl. No. 10/712,813.
U.S. Appl. No. 10/762,409.
U.S. Appl. No. 10/909,593.

* cited by examiner

APPARATUS AND METHOD FOR PROVIDING A FLUID CUT MEASUREMENT OF A MULTI-LIQUID MIXTURE COMPENSATED FOR ENTRAINED GAS

CROSS-REFERENCE TO RELATED APPLICATIONS

The present application claims the benefit of U.S. Provisional Patent Application No. 60/654,355, filed Feb. 18, 2005, and U.S. Provisional Patent Application No. 60/610,450, filed Sep. 16, 2004, which are all incorporated herein by reference.

BACKGROUND

The present disclosure relates to an apparatus for measuring a multi-fluid flow having entrained gas therein, and more particularly to an apparatus that measures the speed of sound propagating through the multi-fluid flow to determine the gas volume fraction of the gas in the process flow and compensating the output measurement of a fluid cut measurement device for entrained gas.

A fluid flow process (flow process) includes any process that involves the flow of fluid through pipe, ducts, or other conduits, as well as through fluid control devices such as pumps, valves, orifices, heat exchangers, and the like. Flow processes are found in many different industries such as the oil and gas industry, refining, food and beverage industry, chemical and petrochemical industry, pulp and paper industry, power generation, pharmaceutical industry, and water and wastewater treatment industry. The fluid within the flow process may be a single phase fluid (e.g., gas, liquid or liquid/liquid mixture) and/or a multi-phase mixture (e.g. paper and pulp slurries or other solid/liquid mixtures). The multi-phase mixture may be a two-phase liquid/gas mixture, a solid/gas mixture or a solid/liquid mixture, gas entrained liquid or a three-phase mixture.

In certain flow processes, such as those found in the oil and gas industries, it is desirable to separate liquid (e.g., oil and/or water) and gas (e.g., air) components of a fluid. This is typically accomplished using a separator, which is an item of production equipment used to separate liquid components of the fluid stream from gaseous components. The liquid and gas components flow from the separator in separate legs (pipes), with the leg containing the gas component referred to as the "gas leg" and the leg containing the liquid component(s) referred to as the "liquid leg".

Driven by goals of reducing size and cost of conventional three phase separation approaches, many operators have adopted approaches that utilize smaller, two-phase, gas/liquid separation in conjunction with flow and water cut measurement to measure net oil. Many techniques are used for gas/liquid separation, including level-controlled batch tank separators and continuous flow cyclonic separators.

Typically, there are three methods widely used to determine water cut and, in turn, net oil: 1) density measurement via a Coriolis meter, 2) frequency of a resonant microwave oscillator, and 3) absorption of microwave energy. Problematically, the presence of free gas in any of these devices can result in significant over-reporting of net oil.

Although most gas/liquid separator-based net oil measurement approaches are designed to eliminate gases in the liquid leg of the separator, it has proved difficult to ensure complete gas/liquid separation. Furthermore, since the fluid exits the separator at, or near, vapor pressure, additional outgassing from the liquid can occur prior to measurement due to pressure losses in the flowing mixture. As a result, errors in oil fraction measurement attributed to the entrained gasses can often be the single largest source of error in net oil measurement.

Thus, there remains a need for an apparatus to compensate for entrained gas within a multi-liquid mixture to provide an accurate fluid cut of the liquids in the mixture.

BRIEF SUMMARY

In one aspect, there is provided an apparatus for providing a fluid cut measurement of a multi-liquid mixture compensated for entrained gas. The apparatus includes a first device configured to sense at least one parameter of the mixture indicative of a fluid cut of a first liquid in the mixture and provide a first output signal indicative of the fluid cut of the first liquid. A second device is configured to determine a concentration of gas in the mixture in response to a speed of sound in the mixture and provide a second output signal indicative of the concentration of the gas; and a signal processor is configured to receive the first and second signals and adjust the fluid cut of the first liquid using the concentration of the gas to determine a compensated fluid cut of the first liquid.

In one embodiment, the parameter of the mixture sensed by the first device includes a density of the mixture, and the signal processor determines the compensated fluid cut using the equation:

$$\Phi_{compensated} = \Phi_{liquid1} - \phi_G \frac{\rho_{liquid2} - \rho_G}{\rho_{liquid2} - \rho_{liquid1}}$$

where: $\Phi_{compensated}$ is the compensated fluid cut of the first liquid, $\Phi_{liquid1}$ is the fluid cut of the first liquid provided by the first device, $\Phi_G$ is the concentration of the gas provided by the second device, $\rho_{liquid1}$ is a density of the first liquid, $\rho_{liquid2}$ is a density of a second liquid in the mixture, and $\rho_G$ is a density of the gas. In this embodiment, the first device may include at least one of a Coriolis meter and a gamma densitometer.

In another embodiment the parameter of the mixture sensed by the first device includes a permittivity of the mixture, and the signal processor determines the compensated fluid cut using the equation:

$$\Phi_{compensated} = \Phi_{liquid1} - \phi_G \frac{\sqrt{\varepsilon_{liquid2}} - \sqrt{\varepsilon_G}}{\sqrt{\varepsilon_{liquid2}} - \sqrt{\varepsilon_{liquid1}}}$$

where: $\Phi_{compensated}$ is the compensated fluid cut of the first liquid, $\Phi_{liquid\,1}$ is the fluid cut of the first liquid provided by the first device, $\Phi_G$ is the concentration of the gas provided by the second device, $\varepsilon_{liquid1}$ is a permittivity of the first liquid, $\varepsilon_{liquid2}$ is a permittivity of a second liquid in the mixture, and $\varepsilon_G$ is a permittivity of the gas. In this embodiment, the first device may include a resonant microwave oscillator.

In yet another embodiment, the parameter of the mixture sensed by the first device includes an amount of microwave energy absorbed by the mixture, and the signal processor determines the compensated fluid cut using the equation:

$$\Phi_{compensated} = \Phi_{liquid\,1} - \Phi_G$$

where: $\Phi_{compensated}$ is the compensated fluid cut of the first liquid, $\Phi_{liquid\ 1}$ is the fluid cut of the first liquid provided by the first device, and $\Phi_G$ is the concentration of the gas. In this embodiment, the fist device may include a microwave absorption watercut meter.

In any of the above embodiments, the second device may include at least two sensors at different axial locations along a pipe through which the mixture flows. Each of the sensors provides a respective pressure signal indicative of a pressure disturbance within the pipe at a corresponding axial position, and the signal processor, responsive to the pressure signals, determines the speed of sound in the mixture.

In another aspect, a method for compensating a fluid cut of a multi-liquid mixture for entrained gas comprises: sensing at least one first parameter of the mixture indicative of a fluid cut of a first liquid in the mixture; determining the fluid cut of the first liquid using the at least one first parameter; sensing at least one second parameter of the mixture indicative of a speed of sound of the mixture; determining a concentration of a gas in the mixture in response to the speed of sound of the mixture; and adjusting the fluid cut of the first liquid using the concentration of the gas to determine a compensated fluid cut of the first liquid.

In one embodiment, the at least one first parameter includes a density of the mixture, and the compensated fluid cut is determined using the equation:

$$\Phi_{compensated} = \Phi_{liquid1} - \phi_G \frac{\rho_{liquid2} - \rho_G}{\rho_{liquid2} - \rho_{liquid1}}$$

where: $\Phi_{compensated}$ is the compensated fluid cut of the first liquid, $\Phi_{liquid1}$ is the fluid cut of the first liquid, $\Phi_G$ is the concentration of the gas, $\rho_{liquid1}$ is a density of the first liquid, $\rho_{liquid2}$ is a density of a second liquid in the mixture, and $\rho_G$ is a density of the gas. In this embodiment, the density of the mixture may be determined using one of a Coriolis meter and a gamma densitometer.

In another embodiment, the at least one first parameter includes a permittivity of the mixture, and the compensated fluid cut is determined using the equation:

$$\Phi_{compensated} = \Phi_{liquid1} - \phi_G \frac{\sqrt{\varepsilon_{liquid2}} - \sqrt{\varepsilon_G}}{\sqrt{\varepsilon_{liquid2}} - \sqrt{\varepsilon_{liquid1}}}$$

where: $\Phi_{compensated}$ is the compensated fluid cut of the first liquid, $\Phi_{liquid\ 1}$ is the fluid cut of the first liquid, $\Phi_G$ is the concentration of the gas, $\varepsilon_{liquid1}$ is a permittivity of the first liquid, $\varepsilon_{liquid2}$ is a permittivity of a second liquid in the mixture, and $\varepsilon_G$ is a permittivity of the gas.

In yet another embodiment, the at least one first parameter includes an amount of microwave energy absorbed by the mixture, and the compensated fluid cut is determined using the equation:

$$\Phi_{compensated} = \Phi_{liquid\ 1} - \Phi_G$$

where: $\Phi_{compensated}$ is the compensated fluid cut of the first liquid, $\Phi_{liquid\ 1}$ is the fluid cut of the first liquid, and $\Phi_G$ is the concentration of the gas.

In any of the above embodiments, the speed of sound in the mixture may be determined using at least two sensors at different axial locations along a pipe through which the mixture flows, wherein each of the pressure sensors providing a respective pressure signal indicative of a pressure disturbance within the pipe at a corresponding axial position, and the speed of sound in the mixture is determined in response to the pressure signals.

BRIEF DESCRIPTION OF THE DRAWING

Referring now to the Drawing wherein like items are numbered alike in the various Figures.

DETAILED DESCRIPTION

Figure 1:
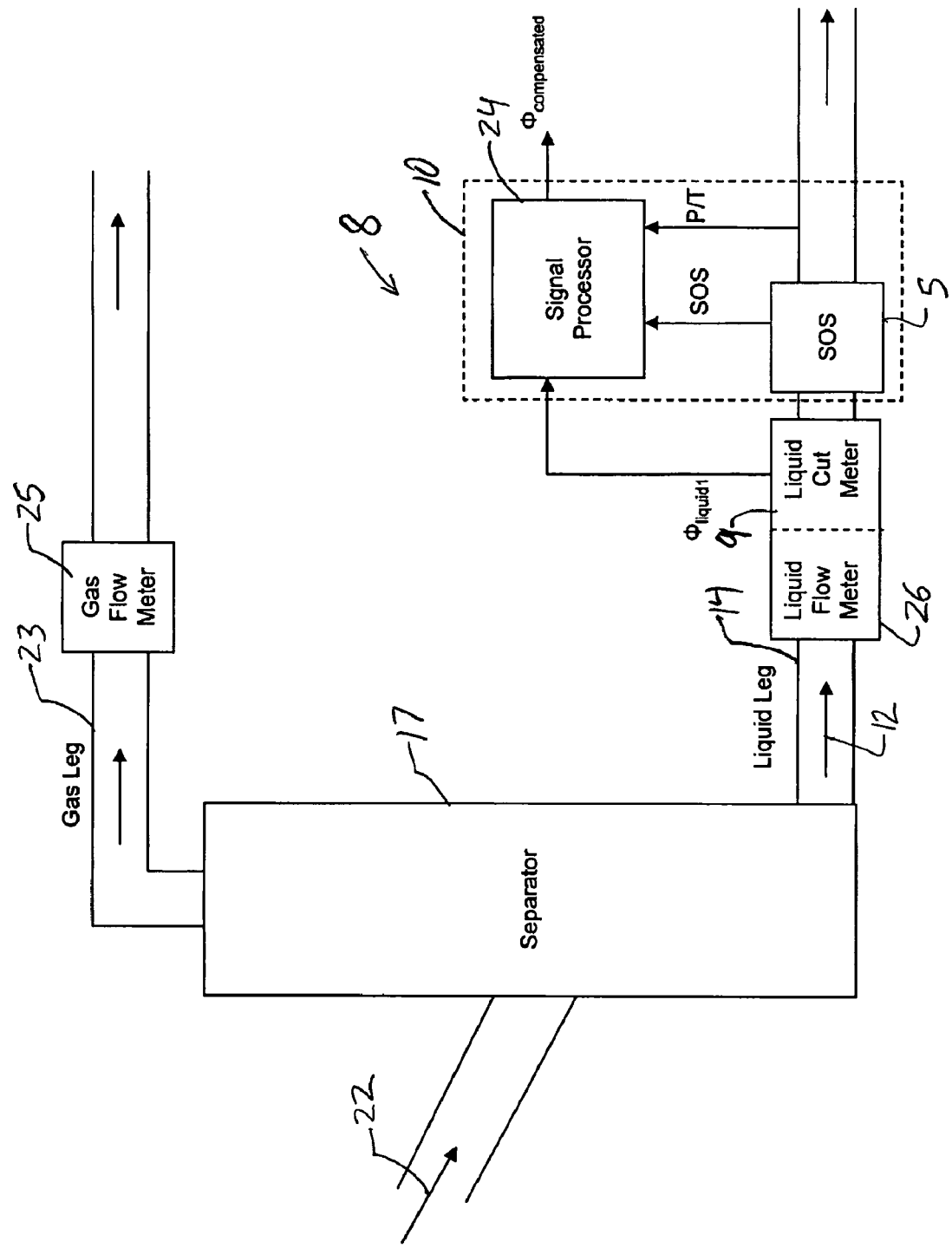
FIG. 1 is a schematic depiction of an apparatus for providing a fluid cut measurement of a multi-liquid mixture compensated for entrained gas.

Referring to FIG. 1, an apparatus for providing a fluid cut measurement of a multi-liquid mixture 12 compensated for entrained gas is shown generally at 8. The apparatus 8 includes a fluid cut measurement device 9 configured to sense at least one parameter of the mixture 12 to determine a fluid cut of a liquid in the multi-liquid mixture flowing in a pipe, duct, channel, conduit, or the like (hereinafter "pipe") 14. The apparatus 8 further includes a gas volume fraction (GVF) measurement device 10 configured to provide real-time measurement of entrained gas in the mixture 12 in response to a measured speed of sound in the mixture 12. Output from the fluid cut device 9 is provided to a signal processor 24, which is configured to adjust the measured fluid cut using the measured GVF to determine a compensated fluid cut of the liquid.

The fluid cut measurement device 9 (also known as a water cut measurement device) may be any typical fluid cut measurement device, such as a Coriolis meter, resonant microwave oscillator, and microwave absorption device. As will be described in further detail hereinafter, different types of fluid cut measurement devices employ different principles of operation, which are differently affected by entrained gas in the mixture. While each type of fluid cut device continues to provide a measurement in the presence of gas, the interpretation of their output can be significantly impacted without specific knowledge of the gas volume fraction. The errors in fluid cut introduced by unrecognized entrained gasses are discussed herein using first-principles relations developed for each type of fluid cut device, and different methods of correction are provided for each of the different types of fluid cut devices to account for the presence of free gas.

In the example shown in FIG. 1, the pipe 14 is depicted as a liquid leg of a gas/liquid separator 17. It is contemplated, however, that the apparatus 8 may be used on any duct, conduit or other form of pipe 14 through which a multi-liquid mixture 12 flows. Also, for simplification of discussion, the multi-liquid mixture 12 is described herein as a water/oil mixture, and various measurements are described as "water cut", "oil cut", and the like. It will be appreciated that the use of water and oil is for purposes of example only, and the apparatus 8 may be used for different multi-liquid mixtures, which may include suspended solids and other non-liquid materials.

The GVF device 10 may employ any technique that measures the sound speed of a fluid. However, it is particularly synergistic with meters such as described in U.S. patent application Ser. No. 10/007,736 filed Nov. 8, 2001, now U.S. Pat. No. 6,889,562, and U.S. patent application Ser. No. 09/729,994, filed Dec. 4, 2004, now U.S. Pat. No. 6,609,069, which are incorporated herein by reference, in that the sound speed measurement, and thus gas volume fraction measurement, can be accomplished using the same hardware as that used for volumetric flow measurement. It should be noted, however, that the gas volume fraction measurement could be performed independently of a volumetric flow measurement, and would have utility as an important process measurement in isolation or in conjunction with other process measurements. U.S. Patent Application Publication No. 2004/0255695 published Dec. 23, 2004, U.S. Patent Application Publication No. 2005/0044929 published Mar. 3, 2005, and U.S. Patent Application Publication No. 2005/0061060 published Mar. 24, 2005, which are all incorporated by reference herein, also describe examples of such meters.

Figure 2:
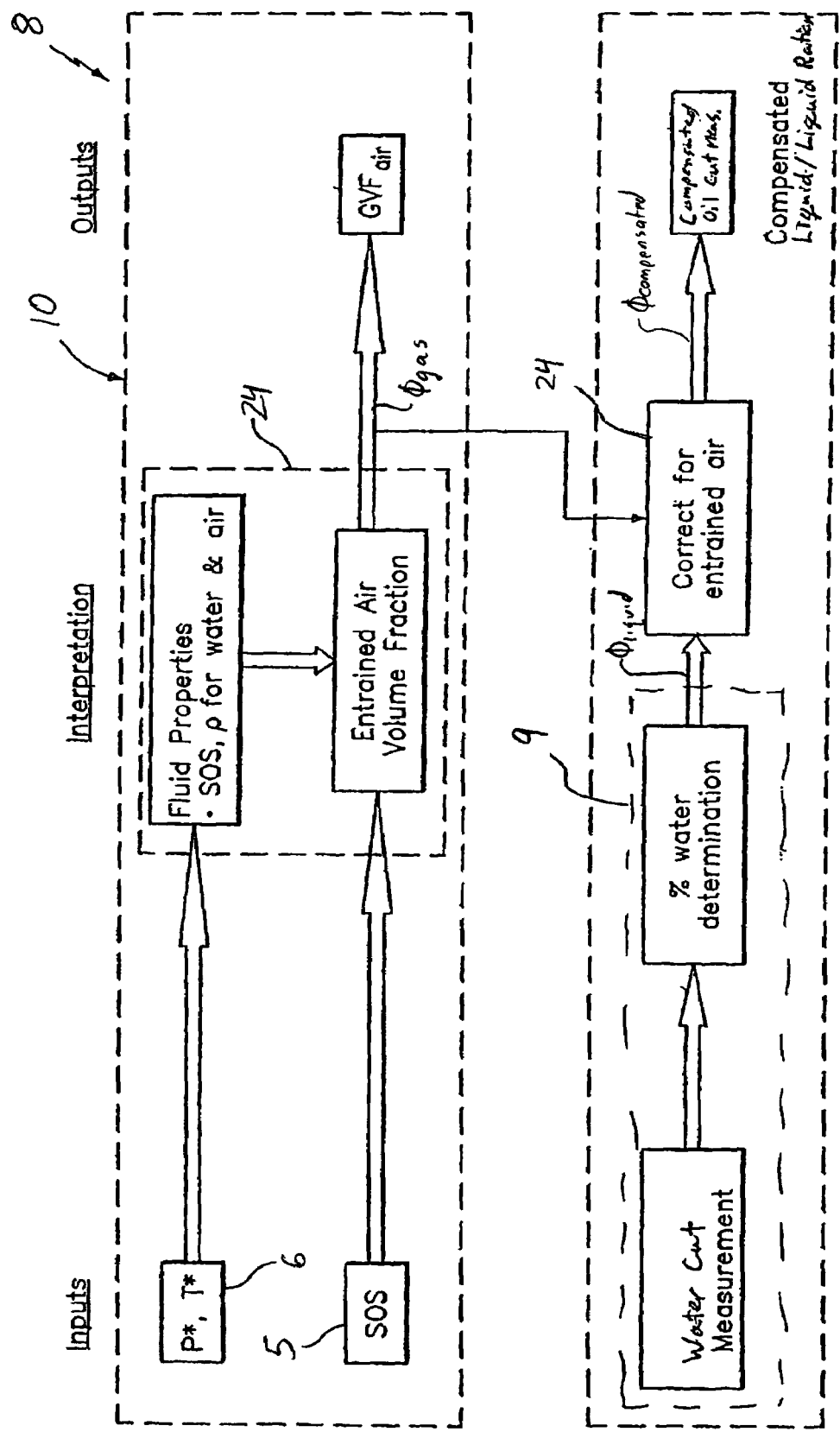
FIG. 2 is a functional flow diagram of a method for compensating the fluid cut measurement using an entrained gas measurement.

FIG. 2 is a block diagram of the apparatus 8 of FIG. 1 that includes the device 5 for measuring the speed of sound propagating with the pipe, and the liquid cut measurement device 9. A pressure sensor and/or temperature sensor 6 measures the pressure and/or temperature of the mixture 12. Alternatively, the pressure and/or temperature may be estimated rather than actually measured. In response to the measured speed of sound, and the pressure and temperature, the signal processor 24 determines the GVF of the mixture 12, as will be described in further detail hereinafter. The fluid cut device 9 provides an output signal indicative of a fluid cut measurement (or a percent water determination) of the fluid flow. As used herein, "fluid cut" is the ratio of a fluid volume in the multi-fluid mixture 12 to total multi-fluid mixture 12 volume. In the signal output by the fluid cut device 9, the fluid cut may be expressed as a simple ratio, a percentage, the ratio of different fluids in the multi-fluid mixture 12, or any function of the ratio of the fluid volume in the mixture 12 to the total mixture 12 volume. The processor 24 processes the gas volume fraction measurement signal and the fluid cut measurement signal to provide a signal indicative of compensated fluid cut of the fluid flow. In the signal output by the fluid cut device 9, the compensated fluid cut may be expressed as a ratio of a fluid volume in the multi-fluid mixture 12 to total multi-fluid mixture 12 volume, a liquid/liquid ratio, or any function of the ratio of the fluid volume in the mixture 12 to the total mixture 12 volume. For example, the signal processor 24 may output a signal indicative of the net volumetric flow rate of one of the fluids in the multi-fluid mixture 12, as will be described in further detail hereinafter.

Figure 3:
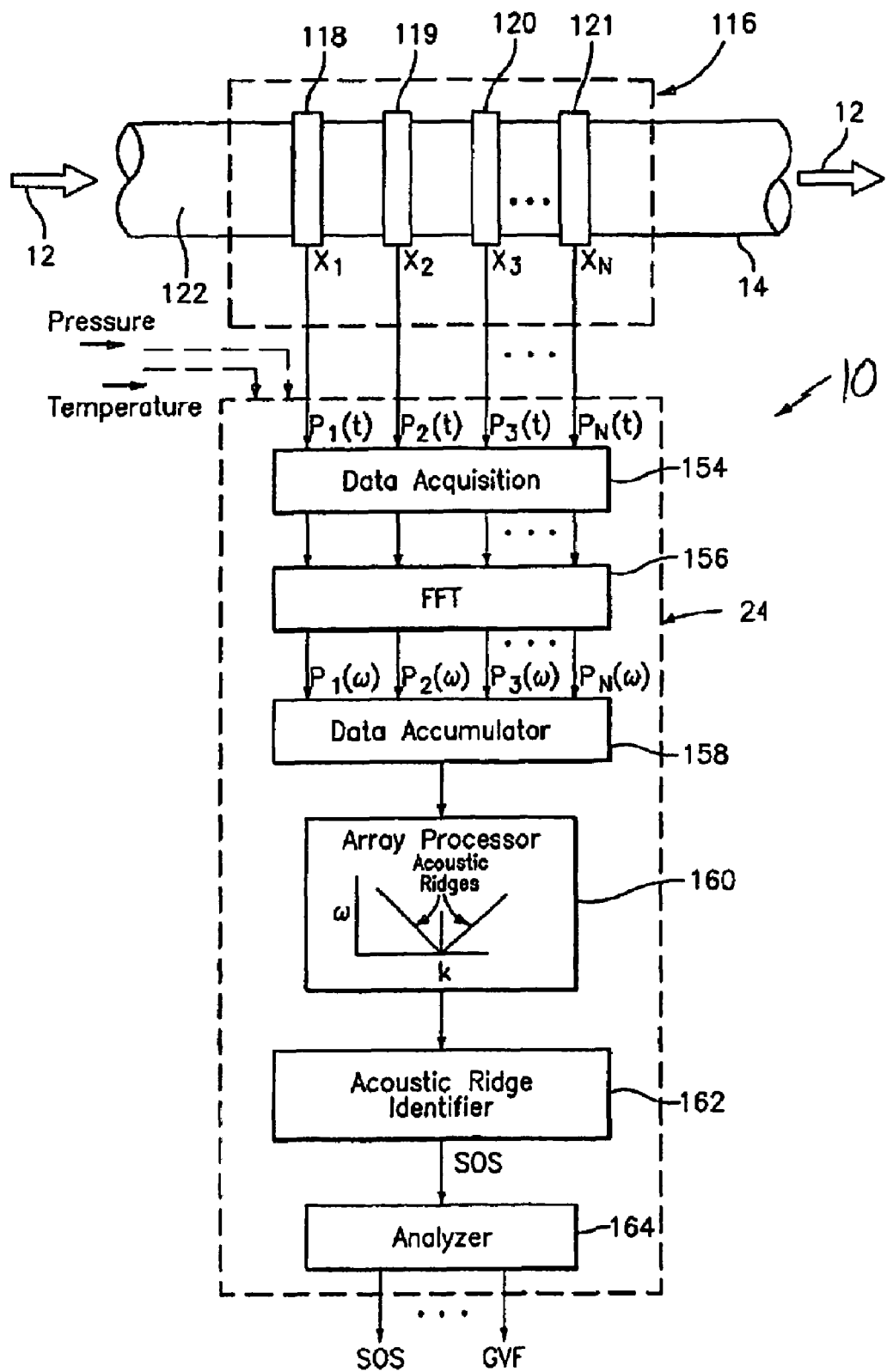
FIG. 3 is a schematic block diagram of a gas volume fraction meter employed in the apparatus of FIG. 1.

FIG. 3 illustrates a gas volume fraction (GVF) meter, as may be used as device 10 of FIG. 1. The GVF meter 10 includes a sensing device 116 disposed on the pipe 14 and a processing unit 124 operably coupled to the sensing device. The sensing device 116 comprises an array of at least two pressure sensors 118,119, located at at least two locations $x_1$ $x_2$ axially along the pipe 14 for sensing respective stochastic signals propagating between the sensors 118,119 within the pipe at their respective locations. Each sensor 118,119 provides a signal indicating an unsteady pressure at the location of the sensor, at each instant in a series of sampling instants.

The sensor array may include more than two pressure sensors as depicted by pressure sensor 120,121 at locations $x_3, x_N$, respectively. The array of sensors of the sensing device 116 may include any number of pressure sensors 118-121 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the mixture. Therefore, the number of sensors used is dependent at least on the degree of accuracy desired and the desired update rate of the output parameter provided by the apparatus 100.

The pressure sensors 118-121 may be clamped onto or generally removably mounted to the pipe by any releasable fastener, such as bolts, screws and clamps. Alternatively, the sensors may be permanently attached to, ported in or integral (e.g., embedded) with the pipe 14.

The device 10 may include one or more acoustic sources 127 to enable the measurement of the speed of sound propagating through the mixture 12 for instances of acoustically quiet flow. The acoustic source may be a device the taps or vibrates on the wall of the pipe, for example. The acoustic sources may be disposed at the input end of output end of the array of sensors 118-121, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, and the turbulent mixture itself.

The pressure generated by the acoustic pressure disturbances is measured through the pressure sensors 118-121, which provide analog pressure time-varying signals $P_1(t)$, $P_2(t), P_3(t), P_N(t)$ to the signal processing unit 124. The processing unit 124 processes the pressure signals to first provide output signals 151,155 indicative of the speed of sound propagating through the flow 12, and subsequently, provide a GVF measurement in response to pressure disturbances generated by acoustic waves propagating through the flow 12.

More specifically, the processing unit 124 receives the pressure signals from the array of sensors 118-121. A data acquisition unit 154 digitizes pressure signals $P_1(t)$-$P_N(t)$ associated with the acoustic waves 14 propagating through the pipe 114. An FFT logic 156 calculates the Fourier transform of the digitized time-based input signals $P_1(t)$-$P_N(t)$ and provide complex frequency domain (or frequency based) signals $P_1(\omega),P_2(\omega),P_3(\omega),P_N(\omega)$ indicative of the frequency content of the input signals.

A data accumulator 158 accumulates the additional signals $P_1(t)$-$P_N(t)$ from the sensors, and provides the data accumulated over a sampling interval to an array processor 160, which performs a spatial-temporal (two-dimensional) transform of the sensor data, from the xt domain to the k-$\omega$ domain, and then calculates the power in the k-$\omega$ plane, as represented by a k-$\omega$ plot, similar to that provided by the convective array processor 146.

To calculate the power in the k-$\omega$ plane, as represented by a k-$\omega$ plot (see FIG. 4) of either the signals or the differenced signals, the array processor 160 determines the wavelength and so the (spatial) wavenumber k, and also the (temporal) frequency and so the angular frequency $\omega$, of various of the spectral components of the stochastic parameter. There are numerous algorithms available in the public domain to perform the spatial/temporal decomposition of arrays of sensor units 118-121.

Figure 4:
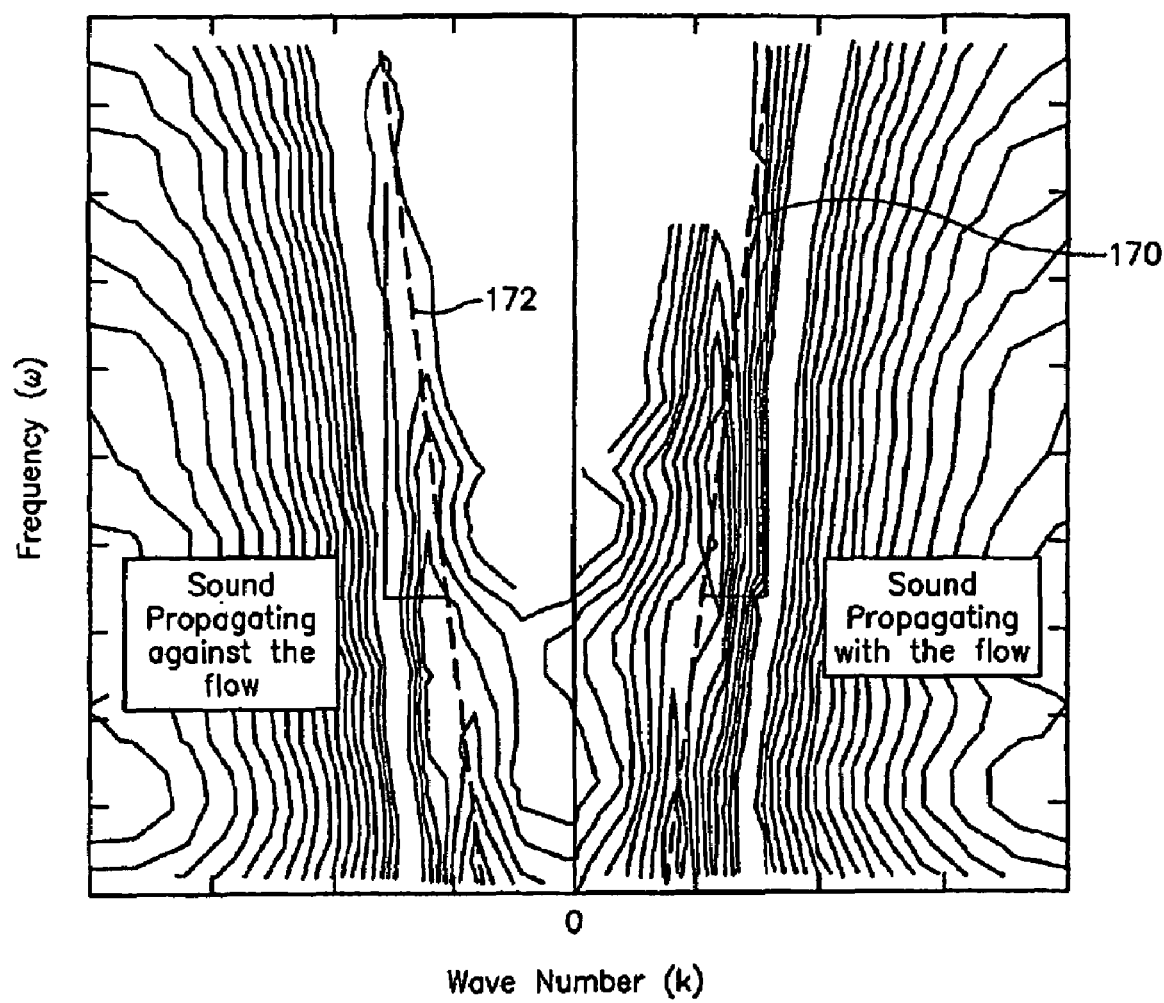
FIG. 4 is a kω plot of data process from an array of pressure sensors used to measure the speed of sound of a fluid flow passing through a pipe.

In the case of suitable acoustic waves being present in both axial directions, the power in the k-$\omega$ plane shown in a k-$\omega$ plot of FIG. 4 so determined will exhibit a structure that is called an acoustic ridge 170,172 in both the left and right planes of the plot, wherein one of the acoustic ridges 170 is indicative of the speed of sound traveling in one axial direction and the other acoustic ridge 172 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-$\omega$ pairs to appear more or less along a line 170,172 with some slope, the slope indicating the speed of sound.

The power in the k-$\omega$ plane so determined is then provided to an acoustic ridge identifier 162, which uses one or another feature extraction method to determine the location and orientation (slope) of any acoustic ridge present in the left and right k-$\omega$ plane. The velocity may be determined by using the slope of one of the two acoustic ridges 170,172 or averaging the slopes of the acoustic ridges 170,172. The velocity may then be used with the pipe 14 inside diameter to calculate a flow rate of the mixture 12.

Finally, information including the acoustic ridge orientation (slope) is used by an analyzer 164 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

An array processor 160 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

One such technique of determining the speed of sound propagating through the flow 12 is using array processing techniques to define an acoustic ridge in the k-$\omega$ plane as shown in FIG. 4. The slope of the acoustic ridge is indicative of the speed of sound propagating through the flow 12. The speed of sound (SOS) is determined by applying sonar arraying processing techniques to determine the speed at which the one dimensional acoustic waves propagate past the axial array of unsteady pressure measurements distributed along the pipe 14.

The device 10 measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and flow 12 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004, now U.S. Pat. No. 7,146,864; U.S. patent application Ser. No. 09/997,221, filed Nov. 28, 2001, now U.S. Pat. No. 6,587,798; U.S. patent application Ser. No. 10/007,749, filed Nov. 7, 2001 now U.S. Pat. No. 6,732,575, and U.S. patent application Ser. No. 10/762,410, filed Jan. 21, 2004, now U.S. Pat. No. 7,062,976 each of which are incorporated herein by reference.

While the GVF meter 10 using an array of sensors 118-121 to measure the speed of sound of an acoustic wave propagating through the mixture is shown and described, one will appreciate that any means for measuring the speed of sound of the acoustic wave may used to determine the entrained gas volume fraction of the mixture 10 or other characteristics of the flow described hereinbefore.

In the present embodiment, the analyzer 164 of the processing unit 124 provides output signals indicative of characteristics of the mixture 12 that are related to the measured speed of sound (SOS) propagating through the mixture 12. For example, to determine the gas volume fraction (or phase fraction), the analyzer 164 assumes a nearly isothermal condition for the mixture 12. As such the gas volume fraction or the void fraction is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}{}^2)$; Rg=gas density, rl=liquid density, $K_{eff}$=effective K (modulus of the liquid and pipewall), P=pressure, and $a_{meas}$=measured speed of sound.

Effectively, $$\text{Gas Volume Fraction (GVF)}=(-B+\text{sqrt}(B^2-4*A*C))/(2*A)$$

Alternatively, the sound speed of a mixture can be related to volumetric phase fraction ($\Phi_i$) of the components and the sound speed (a) and densities ($\rho$) of the component through the Wood equation.

$$\frac{1}{\rho_{mix} a_{mix\infty}^2} = \sum_{i=1}^{N} \frac{\phi_i}{\rho_i a_i^2} \quad \text{where} \quad \rho_{mix} = \sum_{i=1}^{N} \rho_i \phi_i \tag{5}$$

For example, the measured density ($\rho_{mix}$) from the first device (e.g., Coriolis meter or gamma densitometer) may be used as an input to this equation.

One dimensional compression waves propagating within the mixture 12 contained within the pipe 14 exert an unsteady internal pressure loading on the pipe 14. The degree to which the pipe 14 displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \cfrac{1}{\sqrt{\cfrac{1}{a_{mix\infty}^2} + \rho_{mix}\cfrac{2R}{Et}}} \qquad (6)$$

Figure 5:
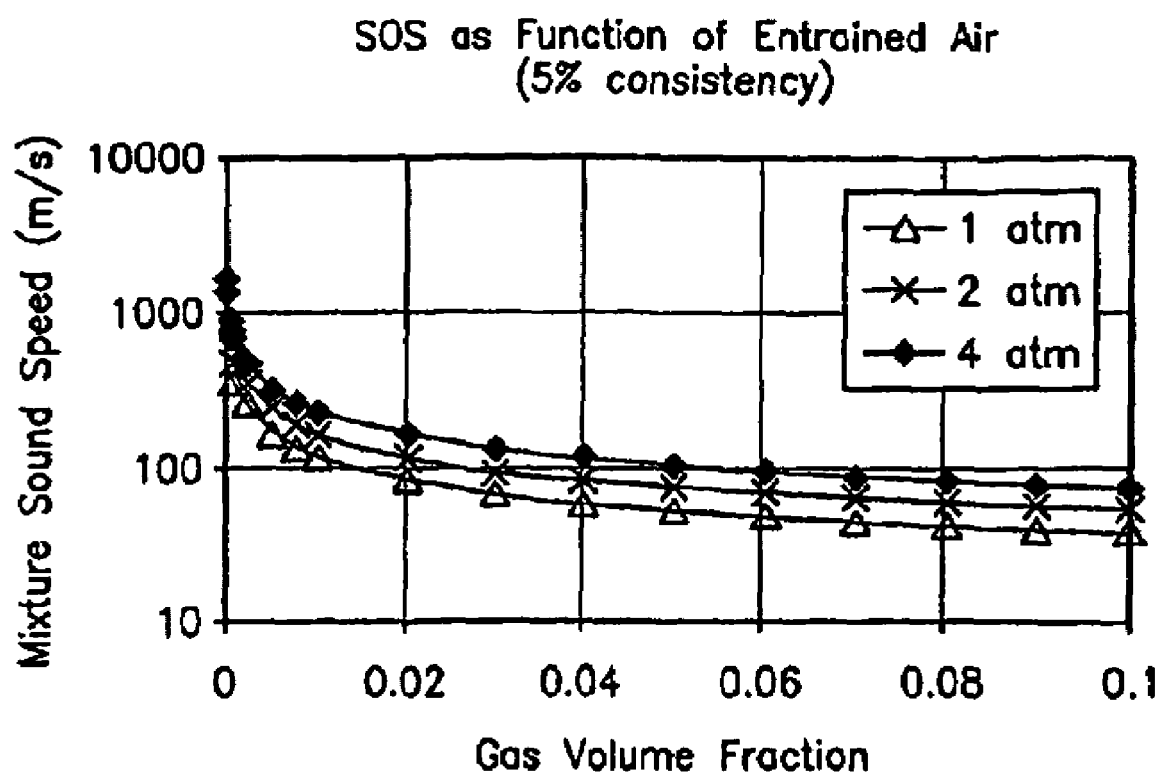
FIG. 5 is a plot of the speed of sound of the fluid flow as a function of the gas volume fraction over a range of different pressures.

The mixing rule essentially states that the compressibility of a mixture ($1/(\rho a^2)$) is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is advantageous to have a good estimate of process pressure to interpret mixture sound speed in terms of volumetric fraction of entrained gas. The effect of process pressure on the relationship between sound speed and entrained gas volume fraction is shown in FIG. 5.

Some or all of the functions within the signal processor 24 may be implemented in software (using a microprocessor or computer) and/or firmware, or may be implemented using analog and/or digital hardware, having sufficient memory, interfaces, and capacity to perform the functions described herein.

The array of sensors 118-121 and signal processor 24 may be used to determine fluid parameters in addition to GVF. For example, as described in U.S. patent application Ser. No. 10/007,736 filed Nov. 8, 2001, now U.S. Pat. No. 6,889,562, and U.S. patent application Ser. No. 09/729,994, filed Dec. 4, 2004, now U.S. Pat. No. 6,609,069, which are incorporated herein by reference, vortical disturbances within a moving fluid (and other disturbances that convect with the flow) create noise, which can be sensed by the array of sensors 118-121. The vortical disturbances move at either the same velocity as the moving fluid, or at a velocity that can be correlated to the velocity of the moving fluid. The correlation can be performed by exploiting what is sometimes called the dispersion relationship associated with convective disturbances (i.e. $\omega$.=uk, where $\omega$ is the angular frequency of the noise created by the vortical disturbance, u is the velocity of the disturbance, and k is the wavenumber of the noise). Convective disturbances in a flowing fluid can be viewed as disturbances that are fixed to the fluid. These disturbances have a spatial variation associated with them. Since the disturbance can be viewed as affixed to the fluid particles, the spatial variations result in temporal variations when sensed by stationary sensors. The spatial wavelength of the disturbances that move with the fluid is thereby linked to the temporal variations observed by the stationary sensors. Array processing techniques may be used to identify this relationship and thereby determine the convection velocity of the fluid. In case of suitable vortical disturbances being present, a k-$\omega$ plot may be developed, which will exhibit a structure that is called a convective ridge. Such a plot will indicate a tendency for k-$\omega$ pairs to appear more or less along a line with some slope, the slope indicating the flow velocity.

In the embodiment of the present invention as shown in FIG. 3, each of the pressure sensors 118-121 may include a piezoelectric film sensor to measure the unsteady pressures of the fluid flow 12 using either technique described hereinbefore. The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., acoustic waves) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,818, U.S. Patent Application, Publication No. 2004-0168522, Published Sep. 2, 2004, U.S. patent application Ser. No. 11/521,627, filed Sep. 14, 2006, which is a continuation in part of U.S. patent application Ser. No. 10/712,833, U.S. Patent Application Publication Number 2004-0168523, Published Sep. 2, 2004, now abandoned, and U.S. patent application Ser. No. 10/795,111, now U.S. Pat. No. 7,146,864 which are incorporated herein by reference.

Another embodiment of the present invention include a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 118-121, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 118-121 of FIG. 3 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 118-121 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application Ser. No. 10/224,821, entitled "Non-Intrusive Fiber Optic Pressure Sensor for Measuring Unsteady Pressures within a Pipe", filed Aug. 21, 2002, now U.S. Pat. No. 6,595,604, which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 115-118 and it may measure the unsteady (or dynamic or ac) pressure variations inside the pipe or tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

While a number of sensor have been described, one will appreciate that any sensor the measures the speed of sound propagating through the fluid may be used with the present invention, including ultrasonic sensors.

Referring again to FIG. 1, the gas/liquid separator 17 is an item of production equipment used to separate liquid components of an incoming fluid stream 22 from gaseous components. The liquid and gas components flow from the separator in separate pipes (legs) 14 and 23, with the leg 14 containing the liquid component and the leg 23 containing the gas component. The gas leg 23 may include a gas flow meter 25, which measures the volumetric flow rate of a gas flowing therethrough. Similarly, the fluid leg 14 include a fluid flow meter 26 that measures the volumetric flow rate of the mixture 12 flowing through the fluid leg 14. The fluid flow meter 26 may be separate from the fluid cut device 9 and the GVF device 10, as is the case where turbine type flow meters are used, or the fluid flow meter 26 may be combined with the fluid cut device 9, as is the case where a Coriolis meter is used, or with the GVF device 10, which may be configured to provide flow measurement as described above.

While the separator 17 is depicted as a vertical vessel, the gas/liquid separator 17 may be any device for separating gas from a multi-fluid mixture. For example, the separator 17 may include a cylindrical or spherical vessel, and may be either horizontally or vertically positioned. Furthermore, the separator 17 may use gravity segregation, centrifugal separation, cyclone separation, or any other known means to accomplish the separation, and may include one or more stages operating in continuous or batch modes.

In multiphase measurement approaches that utilize gas/liquid separators, net oil volumetric flow rate, $Q_{NO}$, is determined by the product of net volumetric flow, Q, which is determined by the fluid flow meter, and oil phase fraction of the liquid leg of the separator, $\phi_O$, $$Q_{NO} = Q \cdot \phi_O$$

Oil phase fraction is determined using fluid cut device. Under the assumption that no gas is present, knowledge of water cut uniquely determines oil cut.

$$\phi_O + \phi_W = 1$$

With gas present, the water fraction, oil fraction, and gas volume fraction sum to unity and the direct, one-to-one relationship between water cut and oil cut is lost.

$$\phi_O + \phi_W + \phi_G = 1$$

In the presence of free gas, net oil production is given by the product of oil fraction of the total mixture of oil, water, and gas times the total volumetric flow rate of the mixture 12.

As previously noted, different types of fluid cut measurement devices employ different principles of operation, which are differently affected by entrained gas in the mixture. While each type of fluid cut device continues to provide a measurement in the presence of gas, the interpretation of their output can be significantly impacted without specific knowledge of the gas volume fraction. The errors in fluid cut introduced by unrecognized entrained gasses, and different methods of correcting these errors, will now be discussed for three different fluid cut devices: density based fluid cut devices, resonant microwave oscillators, and microwave absorption devices.

Density Based Fluid Cut Devices

Density based fluid cut devices, such as Coriolis meters, are widely used in net oil measurement. Since these meters provide both mass flow and density, they are well-suited for net oil measurements. Although the performance of Coriolis meters in the presence of entrained gases is, in general, dependent on its design parameters, it is assumed that the Coriolis meters considered herein provide accurate mixture mass flow and density for the liquid and slightly aerated liquids. The present embodiment is particularly useful for use with U-tube Coriolis meters, which have been demonstrated to accurately report mass flow and density on aerated mixtures. However, it will be appreciated that the present embodiment may be used with straight tube Coriolis meters and other types of density based fluid cut devices.

Using a Coriolis meter, net oil rate is determined by first by calculating the gross volumetric rate from the ratio of measured mass flow rate and measured density. In the absence of free gas, oil cut of oil/water mixtures is related to the mixture density through knowledge of the single component oil and water densities.

$$\phi_O^* = \frac{\rho_W - \rho_{mixture}}{\rho_W - \rho_O}$$

Here the asterisk is used to define oil cut and water cut inferred from measurements assuming no gas is present. The water cut is related to the oil cut through the assumption that the two components occupy the pipe:

$$\phi_W^* = 1 - \phi_O^* = \frac{\rho_{mixture} - \rho_O}{\rho_W - \rho_O}$$

The effect of free gas on density-based, oil-cut determination can be assessed by expanding the interpretation of density to include a three-component mixture of oil, water, and gas. The density of an N-component mixture is given by a volumetrically-weighted average of the individual component densities. For oil, water and gas mixtures, mixture density is thus given by:

$$\rho_{mixture} = \phi_O \rho_O + \phi_W \rho_W + \phi_G \rho_G$$

with $\phi_O + \phi_W + \phi_G = 1$

Where O, W and G subscripts refer to oil, water and gas, respectively.

Using these definitions, the oil fraction can be shown to be a function of the measured mixture density, the pure component oil and water densities, as well as the gas volume fraction.

$$\phi_O = \frac{\rho_W - \rho_{mixture} + \phi_G(\rho_W - \rho_G)}{\rho_W - \rho_O}$$

Comparing this expression for oil fraction, $\Phi_O$, to that derived assuming only oil and water are present, $\Phi^*_O$, shows how the presence of gas results in an over prediction of net oil.

$$\phi_O = \phi_O^* - \phi_G \frac{\rho_W - \rho_G}{\rho_W - \rho_O}$$

Figure 6:
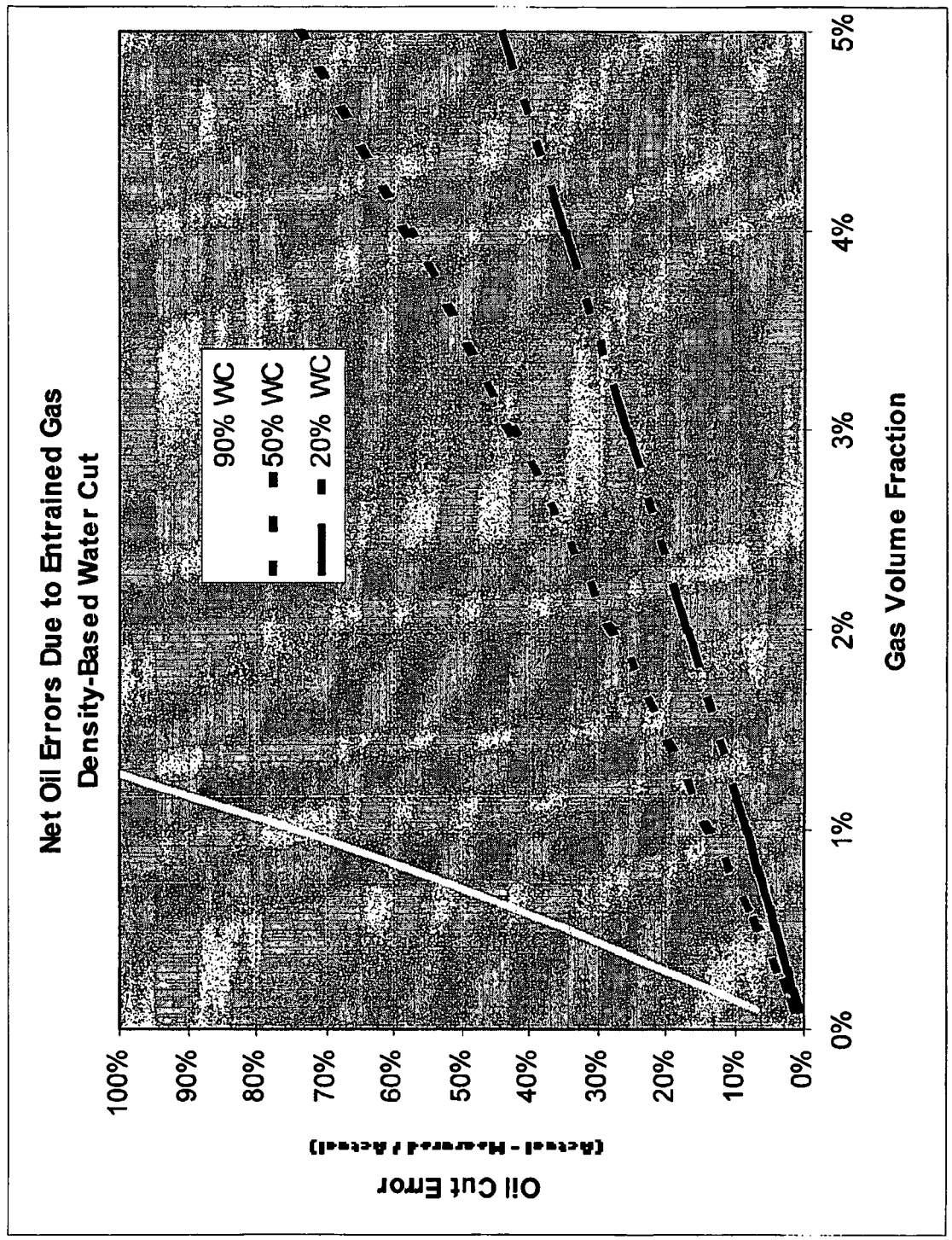
FIG. 6 is a plot depicting the effect of free gas on interpreted oil cut using a density-based water cut measurement.

FIG. 6 shows the error in interpreted oil fraction of the liquid stream due to the presence of a relatively small, but unknown, amount of entrained gas in oil/water stream. The example considers oil with a specific gravity of 0.85 and the water a specific gravity of 1. As discussed above, it is assumed that the coriolis meter accurately reports mixture density and the densities of the oil, water, and gas phases are known.

As shown in FIG. 6, the presence of the free gas has a significant impact on the interpreted oil cut of the liquid stream, and hence net oil. Although still significant at low water cuts, the impact of entrained gases dominates the measurement at high water cuts. As shown, 1% entrained gas results in an approximately 2× over-reporting of net oil at 90% watercut. These errors are removed if the free gas is accurately measured and accounted for when calculating the oil fraction.

Using the relationship discussed above, the following correction factor can be summed directly with the output of the fluid cut meter (FIG. 1 and FIG. 2) to yield a more accurate determination of the oil cut in the presence of free gas.

$$-\phi_G \frac{\rho_W - \rho_G}{\rho_W - \rho_O}$$

This correction factor can be applied by the signal processor 24 of FIG. 1 as the equation:

$$\Phi_{compensated} = \Phi_{liquid1} - \phi_G \frac{\rho_{liquid2} - \rho_G}{\rho_{liquid2} - \rho_{liquid1}}$$

where: $\Phi_{compensated}$ is the compensated fluid cut of the first liquid, $\Phi_{liquid1}$ is the fluid cut of the liquid provided by the fluid cut measurement device 9, $\Phi_G$ is the concentration of the gas provided by the GVF measurement device 10, $\rho_{liquid1}$ is a density of the first liquid, $\rho_{liquid2}$ is a density of a second liquid in the mixture, and $\rho_G$ is a density of the gas. The constants $\rho_{liquid1}$, and $\rho_{liquid2}$, are common to those required for base line calibration of the Coriolis meter. The constant $\rho_G$ may be estimated.

Resonant Microwave Oscillator Fluid Cut Devices

Resonant microwave oscillators leverage the difference in relative permittivity between oil and water to determine water cut. Relative permittivity of a medium, $\epsilon_i$, can be viewed as a measure of speed at which microwaves propagate through a given medium, $V_i$, compared to the speed of microwaves in a vacuum, c.

$$V_i = \frac{c}{\sqrt{\epsilon_i}}$$

Thus, the speed of propagation of microwaves decreases in media with increasing permittivity. For multi-component mixtures, the average propagation velocity is a volumetrically-weighted function of the propagation velocities of the components.

$$V_{mix} = \frac{1}{\sum \frac{\phi_i}{V_i}} = \frac{c}{\sum \phi_i \sqrt{\epsilon_i}}$$

Water typically has a relative permittivity of 68-80, with crude oil typically ranging from 2.2 to 2.6. Since the water phase has the largest relative permittivity, microwave propagation velocity decreases with increasing water cut.

For a fixed geometry resonant cavity, the resonant frequency is proportional to speed of propagation of microwaves inside the cavity. Thus, for a cavity filled with a mixture of oil and water, increasing water cut, decreases the propagation speed, and in turn, decreases the resonant frequency. Thus, once calibrated, the frequency of the resonant microwave cavity is a measure of the speed of propagation and thus the relative permittivity of the mixture inside the cavity, $\epsilon_{mix}$. The oil cut of a oil/water mixture is related to the measured permittivity and the permittivities of the water and oil components:

$$\phi_O^* = \frac{\sqrt{\epsilon_W} - \sqrt{\epsilon_{mixture}}}{\sqrt{\epsilon_W} - \sqrt{\epsilon_O}}$$

Again, under the no gas assumption, there is a direct relation between the interpreted oil cut and water cut.

$$\phi_W^* = 1 - \phi_O^* = \frac{\sqrt{\epsilon_{mixture}} - \sqrt{\epsilon_O}}{\sqrt{\epsilon_W} - \sqrt{\epsilon_O}}$$

Similar to density-based watercut devices, resonant microwave oscillators continue to operate in the presence of gas, with their ability to independently determine watercut degraded. The effect of gas can be incorporated by allowing for the presence of a third component in the analysis. Gas has a relative permittivity of ~1, an as such, free gas appears similar to oil and results in the resonant microwave oscillator over-reporting the actual oil cut.

Using the above relations, the relationship between the actual oil cut, $\Phi_O$, and that interpreted assuming no gas, $\Phi_O^*$, is given below.

$$\phi_O = \phi_O^* - \phi_G \frac{\sqrt{\epsilon_W} - \sqrt{\epsilon_G}}{\sqrt{\epsilon_W} - \sqrt{\epsilon_O}}$$

Figure 7:
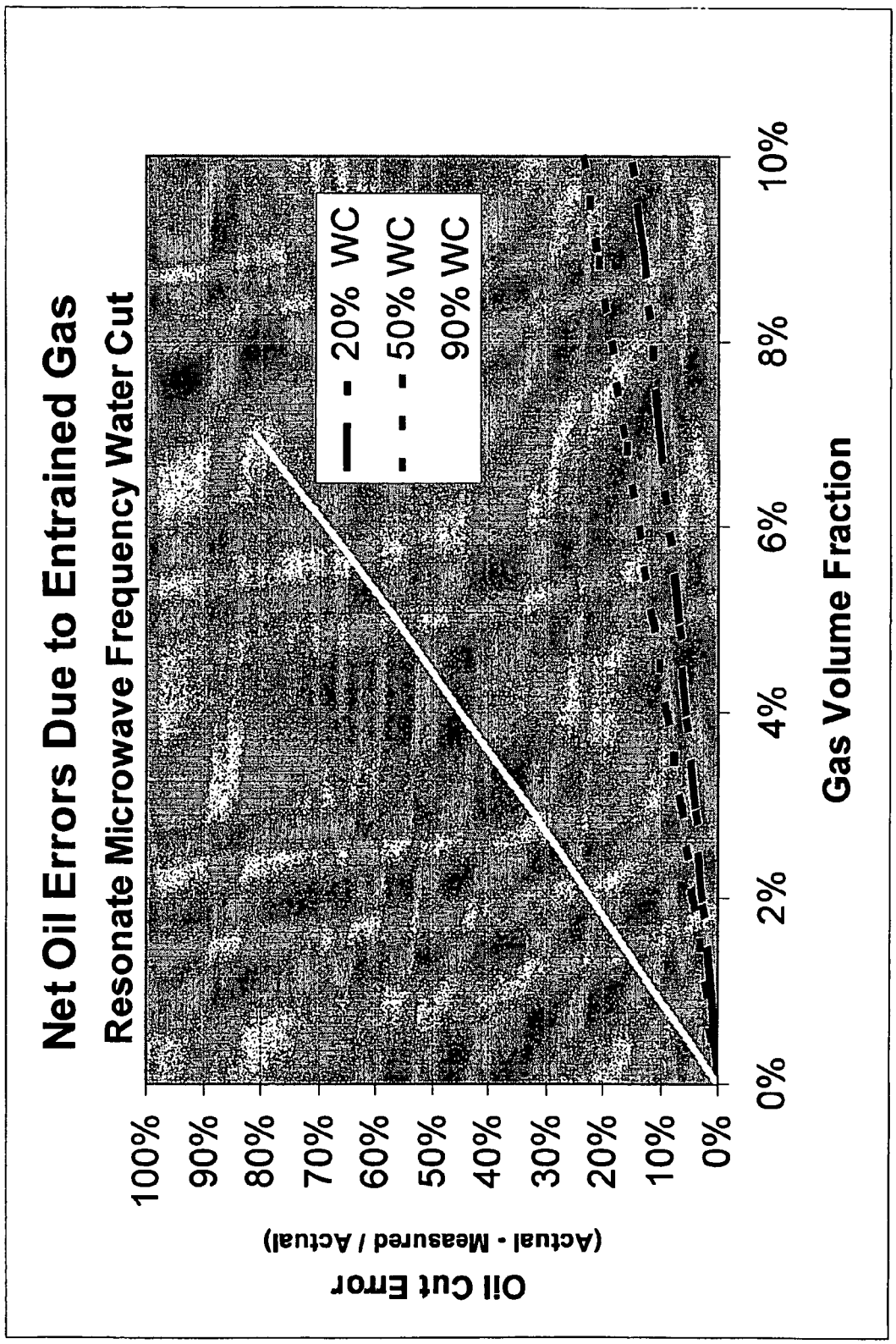
FIG. 7 is a plot depicting the effect of free gas on interpreted oil cut using a resonant microwave cavity device.

FIG. 7 shows the error in interpreted net oil cut that would be incurred by a resonant microwave oscillator due to the presence of a small, but unknown, amount of gas. The relative permittivity of the water, oil and gas phases were assumed to be 66, 2.2, and 1 respectively, in this example. The error is calculated using the equation developed above. The predicted errors, as functions of water cut and gas volume fraction, are broadly consistent with those given in the literature. Although the resonant microwave oscillators are typically less sensitive to free air than density based devices, the effect on net oil can be significant, with the largest proportional errors due to unrecognized free gas occurring at the highest water cuts. These errors are removed if the free gas is accurately measured and accounted for when calculating the oil fraction.

Using the relationship discussed above, the following correction factor can be summed directly with the output of the fluid cut meter (FIG. 1 and FIG. 2) to yield a more accurate determination of the oil cut in the presence of free gas.

$$-\phi_G \frac{\sqrt{\epsilon_W} - \sqrt{\epsilon_G}}{\sqrt{\epsilon_W} - \sqrt{\epsilon_O}}$$

This correction factor can be applied by the signal processor 24 of FIG. 1 as the equation:

$$\Phi_{compensated} = \Phi_{liquid1} - \phi_G \frac{\sqrt{\epsilon_{liquid2}} - \sqrt{\epsilon_G}}{\sqrt{\epsilon_{liquid2}} - \sqrt{\epsilon_{liquid1}}}$$

where: $\Phi_{compensated}$ is the compensated fluid cut of the liquid, $\Phi_{liquid\ 1}$ is the fluid cut of the liquid provided by the fluid cut device 9, $\Phi_G$ is the concentration of the gas provided by the GVF device 10, $\epsilon_{liquid1}$ is a permittivity of the first liquid, $\epsilon_{liquid2}$ is a permittivity of a second liquid in the mixture, and $\epsilon_G$ is a permittivity of the gas. The constants $\epsilon_{liquid1}$, and $\epsilon_{liquid2}$, are common to those required for base line calibration of resonant microwave oscillating devices. The constant $\epsilon_G$ may be estimated.

Microwave Absorption Fluid Cut Devices

The third type of fluid cut device considered is the microwave absorption fluid cut device. Water molecules efficiently absorb microwave energy, whereas hydrocarbons typically do not. Thus, the amount of microwave energy absorbed by a given volume of a mixture of hydrocarbons and water is primarily determined by the water cut of the mixture. Thus, water cut can be determine by a calibrated measure of microwave absorption, α, as follows:

$$\phi^*_W = F(\alpha)$$

Again, assuming no gas is present, oil cut is determined directly from the water cut.

$$\phi^*_O = 1 - \phi^*_W = F(\alpha)$$

From a microwave absorption perspective, gas and crude oil are both, non-absorbing components. Therefore, a microwave absorption device will continue to accurately report water cut (i.e. water fraction) in an oil/water mixture with a small but unknown amount of gas. However, although the water cut is reported accurately, the presence of gas still can result in significant over-reporting of net oil cut.

$$\Phi_O = 1 - \Phi_W - \Phi_G = 1 - F(\alpha) - \Phi_G = \Phi^*_O - \Phi_G$$

Figure 8:
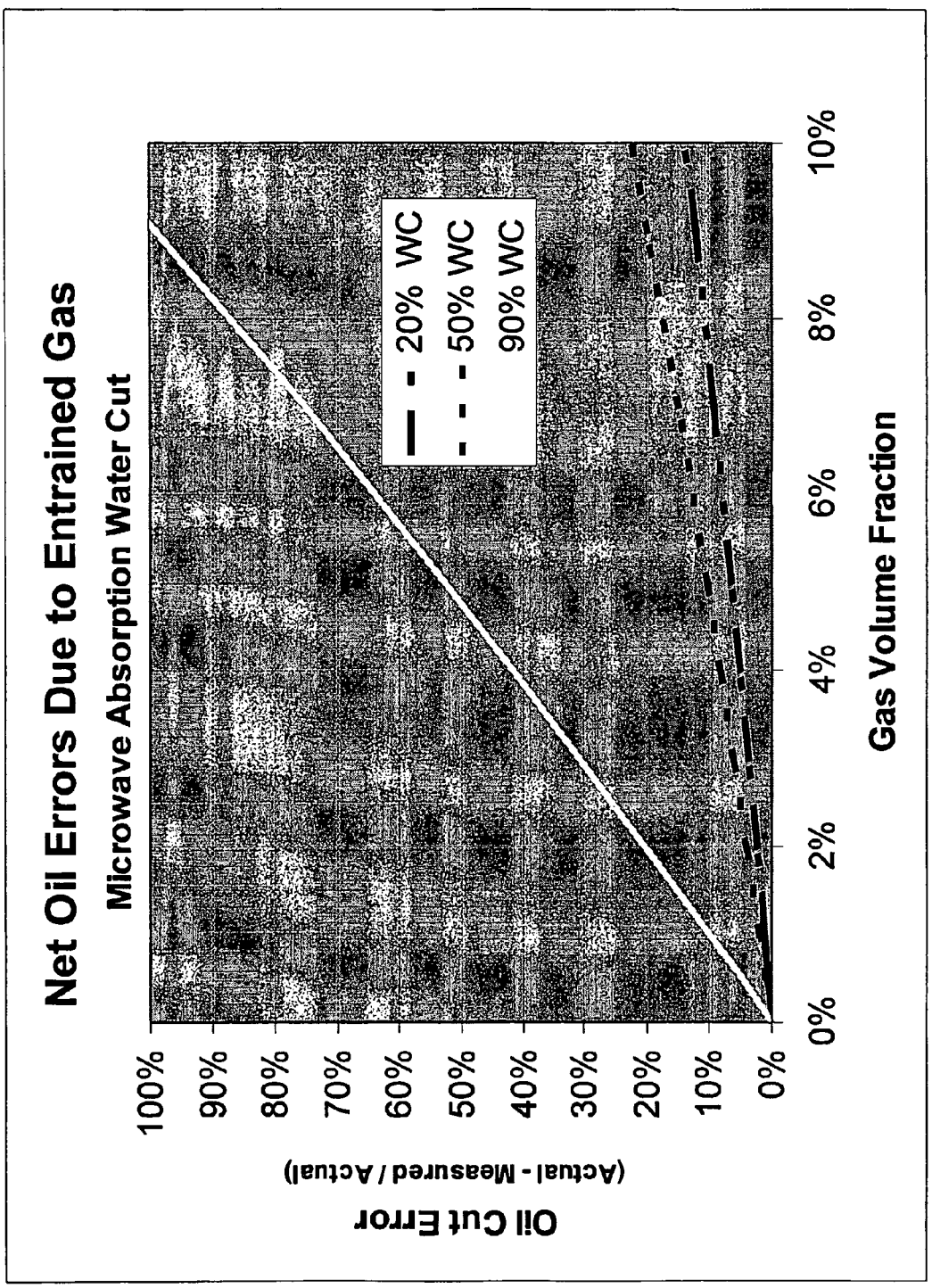
FIG. 8 is a plot depicting the effect of free gas on interpreted oil cut using a microwave absorption device.

For example, consider a non-aerated 90% water, 10% oil stream. A properly calibrated microwave device would accurately report 90% water cut. If this same liquid mixture is then aerated with 10% entrained gas, the resulting mixture would then consist of 81% water, 9% oil and 10% gas by volume. A microwave absorption device would then accurately report a water cut of 81%. However, without knowledge of the amount of gas present, one would then conclude that the mixture was 19% oil, resulting in a nearly 2× over reporting of the oil cut of the stream. FIG. 8 shows the errors in oil cut interpreted using an absorption-based microwave device due to an unrecognized presence of gas as a function gas volume fraction for a range of water cuts. These errors are removed if the free gas is accurately measured and accounted for when calculating the oil fraction.

Using the relationship discussed above, the following correction factor can be summed directly with the output of the fluid cut meter (FIG. 1 and FIG. 2) to yield a more accurate determination of the oil cut in the presence of free gas.

$$-\Phi_G$$

This correction factor can be applied by the signal processor 24 of FIG. 1 as the equation:

$$\Phi_{compensated} = \Phi_{liquid\ 1} - \Phi_G$$

where: $\Phi_{compensated}$ is the compensated fluid cut of the first liquid, $\Phi_{liquid\ 1}$ is the fluid cut of the liquid provided by the fluid cut device 9, and $\Phi_G$ is the concentration of the gas provided by the GVF device 10.

EXAMPLES

Example 1

Experiments were conducted to verify the ability to accurately measure the density of aerated mixtures using the combination of coriolis density and gas fraction measurements. The test consisted of a water flow loop with a 2-inch Micro Motion CMF200 coriolis meter installed in a vertical upward flowing orientation ("flag" mount) with a gas volume fraction meter and pressure sensor installed just downstream of the coriolis outlet. Air was injected upstream of the test section.

Figure 9:
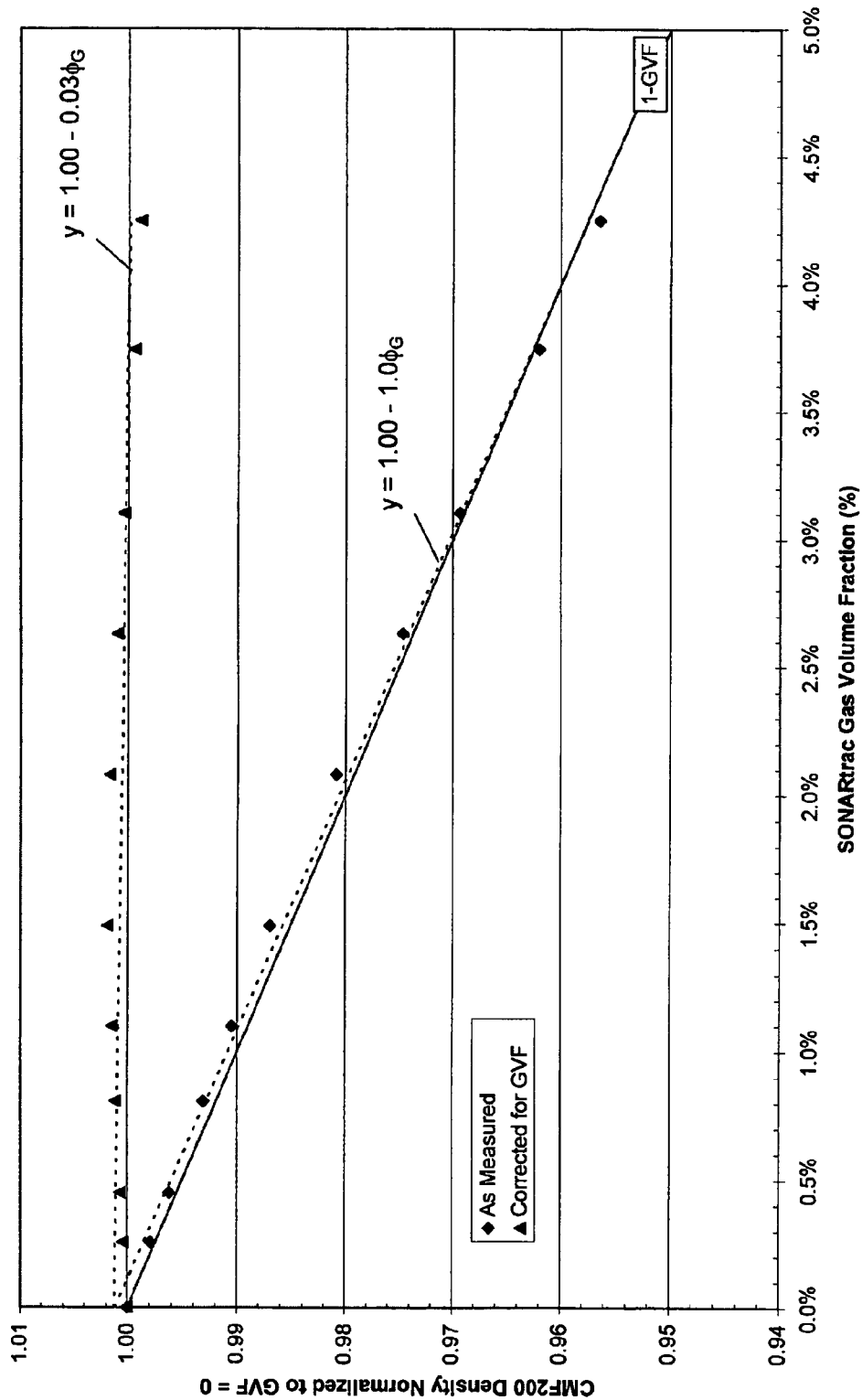
FIG. 9 is a plot depicting the density of aerated water as a function of gas volume fraction as reported by a Coriolis meter with GVF measurement.

FIG. 9 shows the measured mixture density and the corrected liquid-density measured by the combination of the coriolis and gas volume fraction meters. The results confirm that 1) the coriolis meters can continue accurately report mixture density in the presence of gas and 2) the real time measurement of gas volume fraction enables the combination to continue to report liquid density.

Example 2

Figure 10:
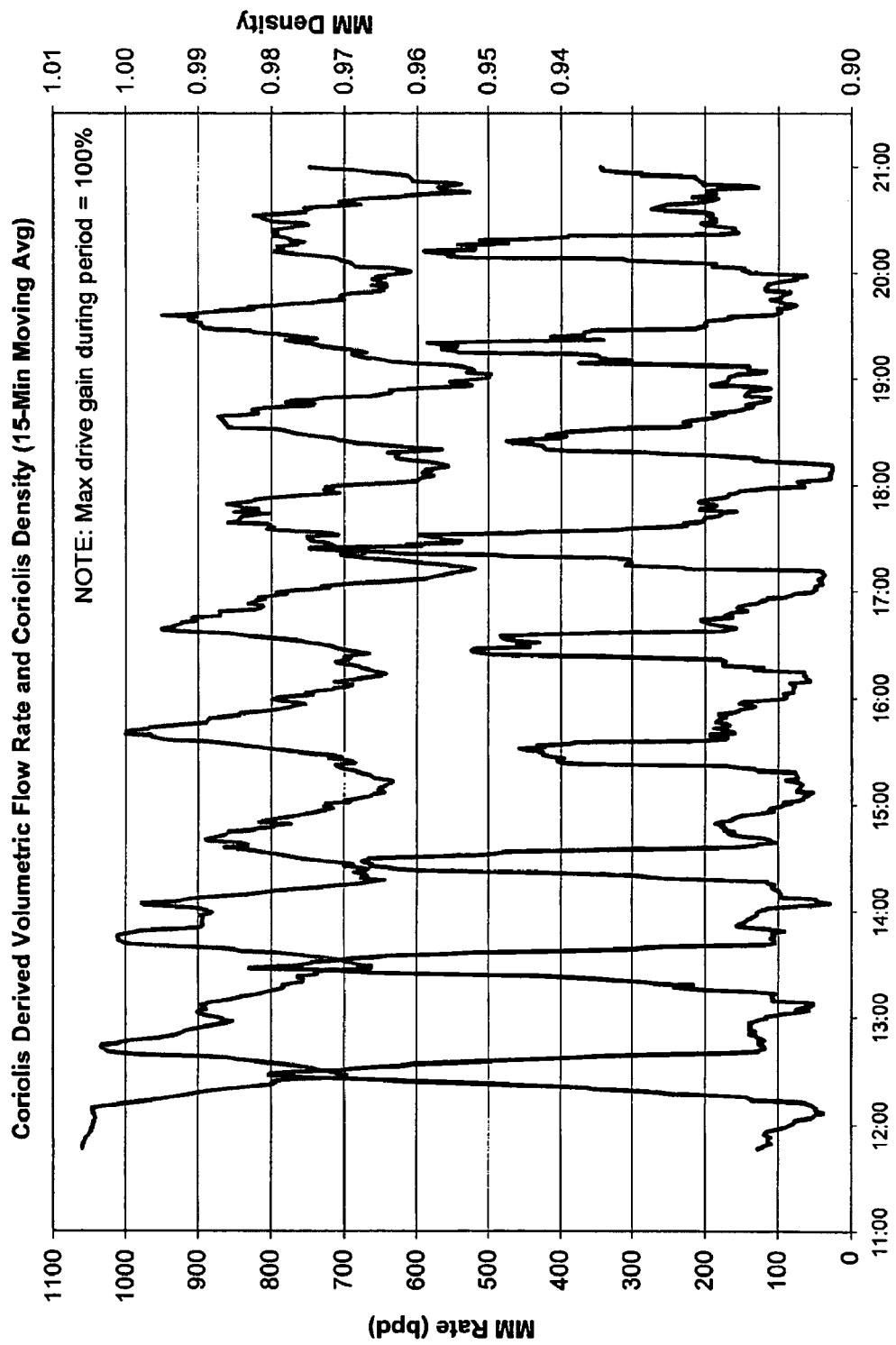
FIG. 10 is a plot depicting the Coriolis mass flow and density reported during a well test.
Figure 11:
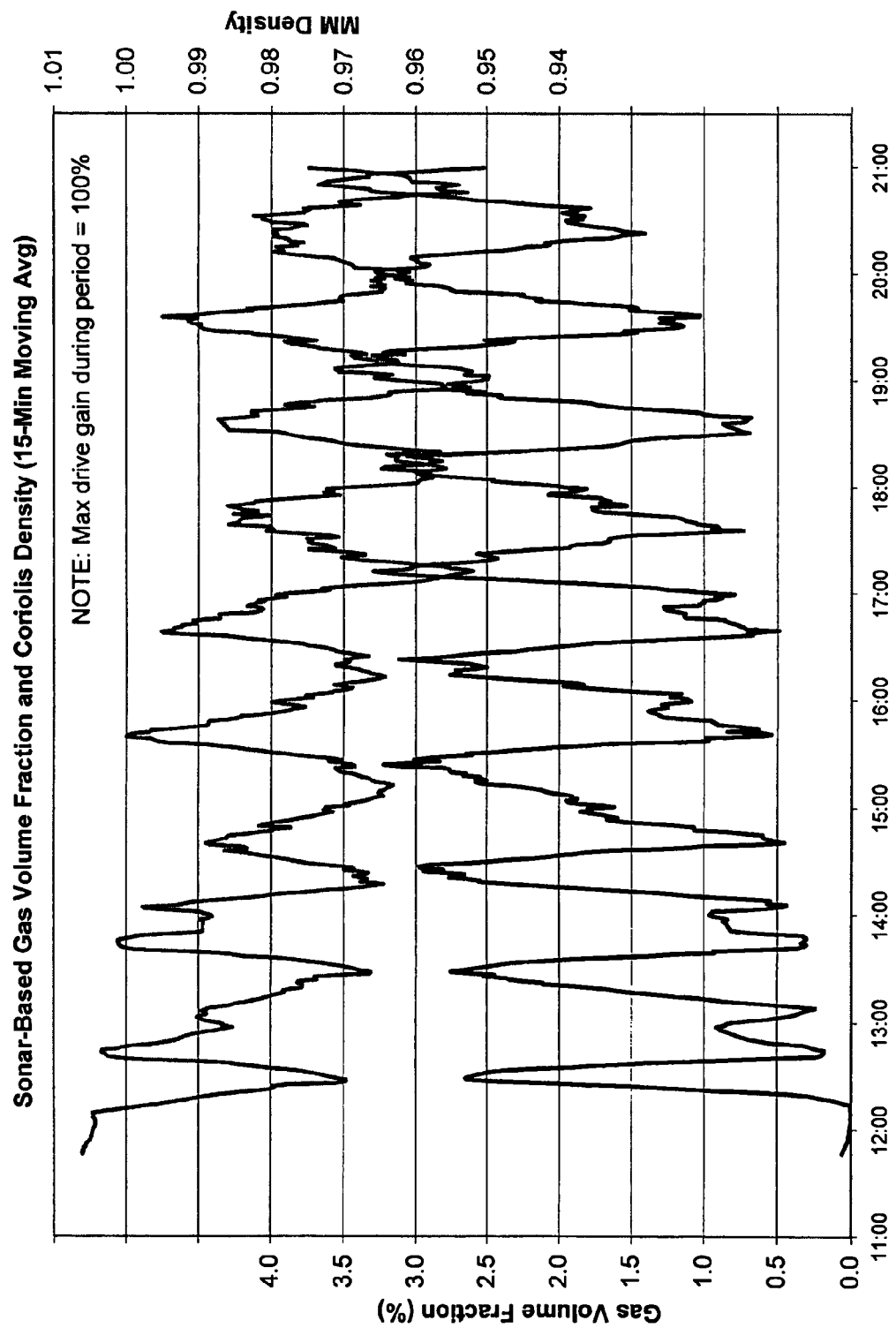
FIG. 11 is a plot depicting the Coriolis density and GVF reported during the well test.

A gas volume fraction meter was installed on the outlet of a coriolis meter on the liquid leg of a continuous-flowing, gas/liquid cylindrical cyclone (GLCC) two-phase separator. Both meters were mounted in a vertical orientation with upward flowing liquid similar to the experimental test section as described above. The mass rate, density and drive gain from the coriolis meter and the gas volume fraction from the gas volume fraction meter were output to a programmable logic controller (PLC) where the data could be stored and later retrieved. The pressure at the outlet of the coriolis meter was also output to the PLC. FIG. 10 shows the gross flow rate and Coriolis measured density during the 9½ hour well test. The gross rate was calculated by dividing the mass flow rate by the density, both directly measured by the Coriolis meter. FIG. 11 shows the measured gas volume fraction and Coriolis measured density. The gas volume fraction ranged from 0 to approximately 4%, varying significantly over the test period.

Figure 12:
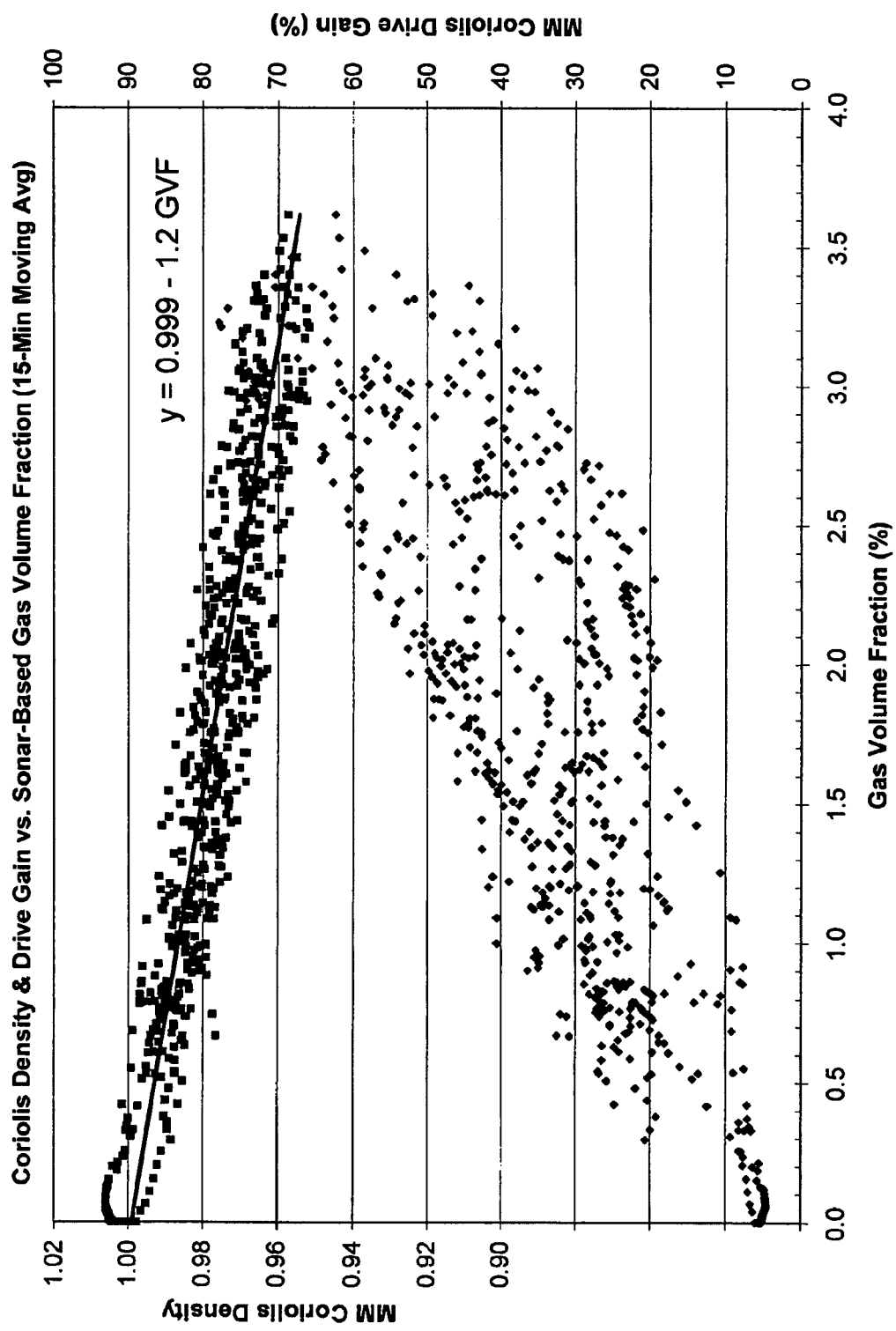
FIG. 12 is a plot depicting the Coriolis density and drive gain plotted vs. GVF during the well test.
Figure 13:
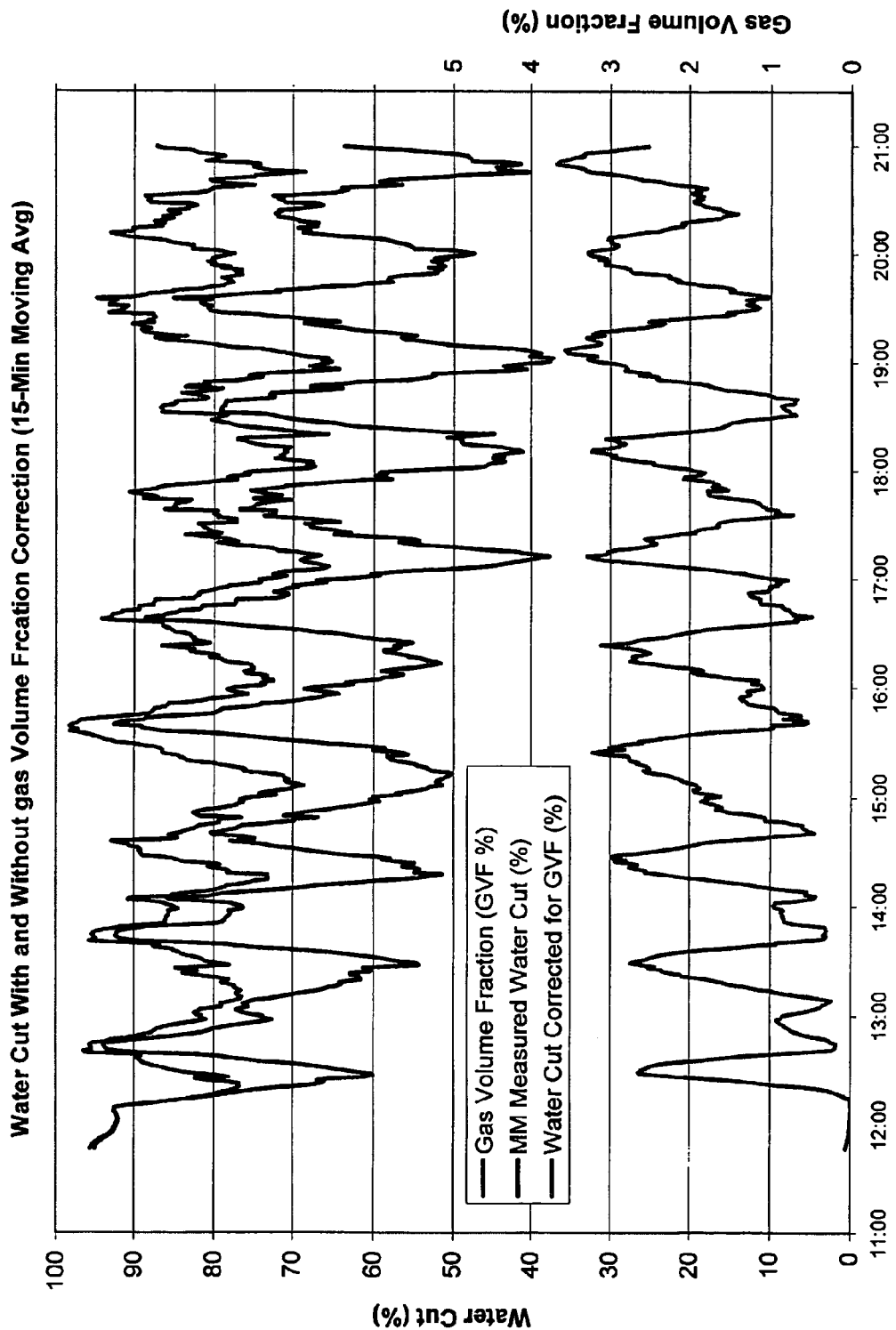
FIG. 13 is a plot depicting the reported and corrected Coriolis water cut and GVF during the well test.

FIG. 12 shows 1) the measured density and 2) the Coriolis drive gain plotted versus gas volume fraction. The measured density and the measured gas volume fraction show good correlation, with the decreases in measured density corresponding to increasing in gas volume fraction. However, unlike the laboratory experiment in which the liquid density was constant, the density of the liquid phase in the well test also varying due to changes water cut throughout the well test period. Time history data (FIG. 11) shows that the gas volume fraction tends to increase with oil fraction. This effect would cause the density of the mixture to decrease more with gas volume fraction than it would if the liquid density were held constant. As shown, a best straight line fit through the data shows a mixture density decreasing at (1.0-1.2-$\Phi_G$), very close to theoretical 1-$\Phi_G$ for liquid/gas mixture with constant liquid properties. The cross-plot of the drive gain versus gas volume fraction shows a qualitative correlation, with the drive gain increasing with increasing gas volume fraction. The water cut with, and without, the knowledge of the gas volume fraction is shown in FIG. 13.

Figure 14:
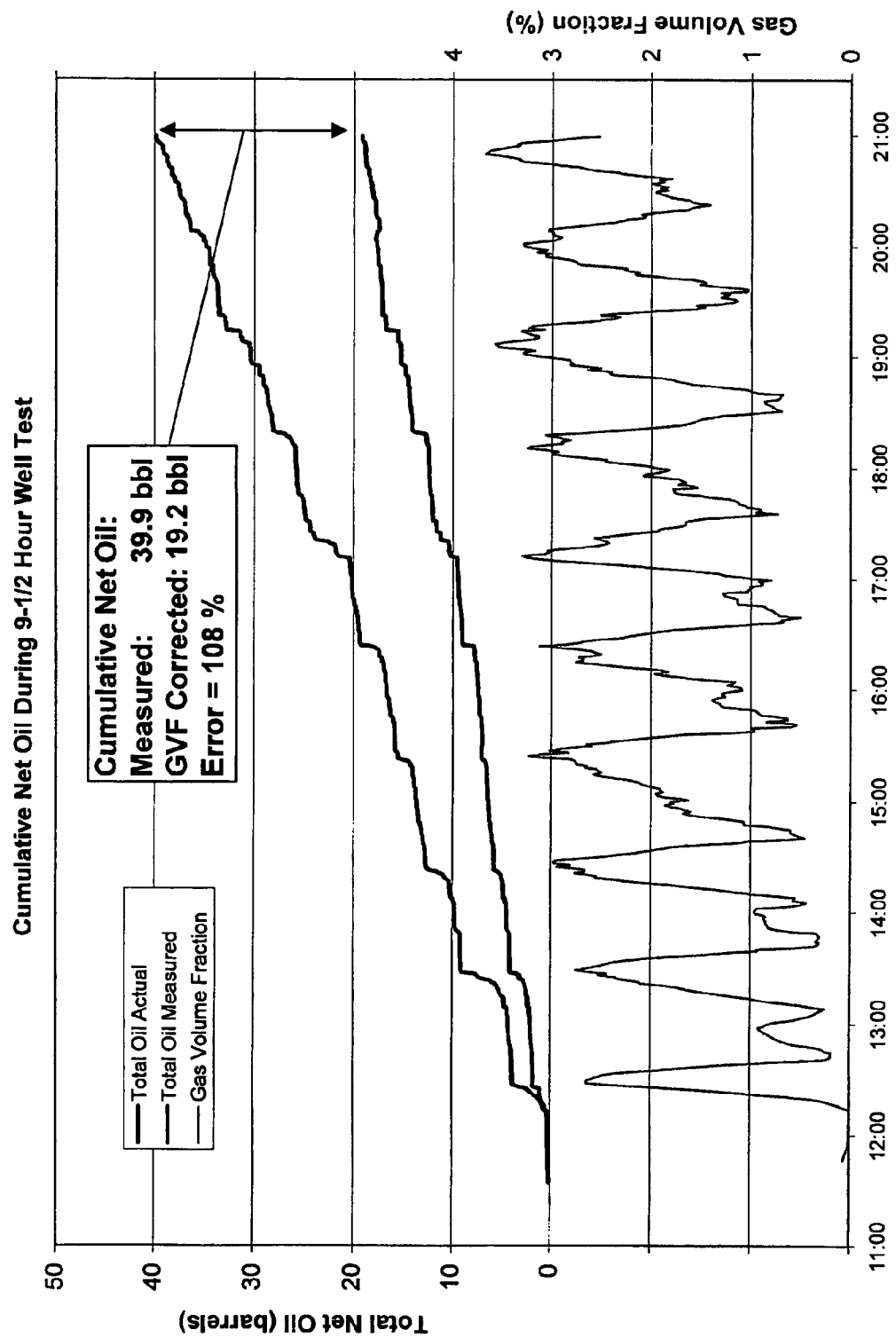
FIG. 14 is a plot depicting the cumulative net oil, reported and corrected, and GVF during the well test.

FIG. 14 shows the cumulative net oil over the well test period for the two cases. Using knowledge of the gas volume fraction when calculating the oil fraction yields a total oil of 19.2 barrels for this 9½ hour well test. If the gas volume fraction were not known an assumed to be negligible, the total oil for this test would be reported as 39.9 barrels. This is an overstatement of the total oil by 20.7 barrels or 108% (FIG. 14).

As shown in the above examples, entrained gases can have a significant impact on the accuracy of net oil measurements. Specifically, net oil measurement determined using a gas/liquid separator in conjunction with a water cut and flow rate measurement on the liquid leg of the separator. The impact of entrained gases was analyzed for three common types of watercut devices, coriolis density meters, microwave resonant cavity devices and microwave attenuation devices. Correction factors to account for the presence of free gas were developed and presented for each device.

Laboratory data confirming the ability of the proposed approach of coupling gas volume fraction meters with watercut devices to provide accurate net oil was presented. The data demonstrates the ability of a combination of gas volume fraction meters and a U-tube Coriolis meter to accurately report liquid density in the presence of 0-5% gas volume fraction.

Well test data from a gas/liquid separation based net oil measurement approach was presented. The data shows the presence of 0-4% free gas in the liquid leg of the separator. Analysis of this data shows that presence of gas resulted in a roughly 2× over-reporting of net oil over the 9½ hour well test period. The present invention provides a method and apparatus to compensate for entrained air within a multi-liquid mixture to provide an accurate liquid cut of the liquids in the mixture.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An apparatus for providing a corrected liquid phase fraction measurement of a first liquid component of a multi-liquid mixture, the multi-liquid mixture flowing through a pipe, and the corrected liquid phase fraction measurement being compensated for entrained gas flowing with the multi-liquid mixture through the pipe, the apparatus comprising:

a first meter that determines at least one parameter of the multi-liquid mixture, the parameter being indicative of an uncorrected liquid phase fraction of the first liquid component and provides a first output signal indicative of the uncorrected liquid phase fraction of the first liquid component;

a second meter that determines a phase fraction of the entrained gas and provides a second output signal indicative of the phase fraction of the entrained gas; and a signal processor, responsive to the first and second output signals for providing the corrected liquid phase fraction measurement of the first liquid component by determining a compensated phase fraction of the first liquid component which is the uncorrected liquid phase fraction of the first liquid component compensated for the entrained gas.

2. The apparatus of claim 1, wherein the multi-liquid mixture includes at least a second fluid component, the parameter sensed by the first meter includes a permittivity of the multi-liquid mixture, and the signal processor determines the corrected liquid phase fraction measurement using the equation:

$$\Phi_{compensated} = \Phi_{liquid\ 1} - \phi_G \frac{\sqrt{\varepsilon_{liquid2}} - \sqrt{\varepsilon_G}}{\sqrt{\varepsilon_{liquid2}} - \sqrt{\varepsilon_{liquid1}}}$$

where: $\Phi_{compensated}$ is the corrected liquid phase fraction measurement of the first liquid component, $\Phi_{liquid\ 1}$ is the uncorrected phase fraction of the first liquid component provided by the first meter, $\Phi_G$ is the phase fraction of the gas provided by the second meter, $\varepsilon_{liquid1}$ is a permittivity of the first liquid component, $\varepsilon_{liquid2}$ is a permittivity of the at the least second liquid component, and $\varepsilon_G$ is a permittivity of the gas.

3. The apparatus of claim 1, wherein the first meter includes a resonant microwave oscillator.

4. The apparatus of claim 1, wherein the multi-liquid mixture includes oil and water and the first liquid component is selected from one of oil and water.

5. The apparatus of claim 1, wherein the second meter includes at least two sensors at different axial locations along a pipe through which the mixture flows, each of the sensors providing a respective pressure signal indicative of a pressure disturbance within the pipe at a corresponding axial position, wherein the signal processor, responsive to the pressure signals, determines the speed of sound propagating though the mixture.

6. The apparatus of claim 1, wherein the at least one parameter determined by the first meter includes the permittivity of the mixture.

7. The apparatus of claim 1, wherein the first meter is a microwave fluid cut meter.

8. The apparatus of claim 1, wherein the first meter is a microwave watercut meter.

9. The apparatus of claim 1, wherein the second meter provides a signal indicative of the phase fraction of the gas in the mixture in response to a speed of sound propagating through the mixture.

10. The apparatus of claim 1, wherein the second meter measures the speed of a one dimensional acoustic wave propagating axially through the mixture.

11. The apparatus of claim 1, wherein the signal processor determines the phase fraction of the gas of the mixture in response to a speed of sound propagating through the mixture.

12. The apparatus of claim 1, wherein the signal processor determines the phase fraction of a second liquid of the mixture, in response the first and second signals.

13. The apparatus of claim 1, wherein the parameter sensed by the first device includes a density of the mixture, and the signal processor determines the compensated fluid cut using the equation:

$$\Phi_{compensated} = \Phi_{liquid1} - \phi_G \frac{\rho_{liquid2} - \rho_G}{\rho_{liquid2} - \rho_{liquid1}}$$

where: $\Phi_{compensated}$ is the compensated fluid cut of the first liquid, $\Phi_{liquid1}$ is the of the first liquid provided by the first device, $\Phi_G$ is the concentration of the gas provided by the second device, $\rho_{liquid1}$ is a density of the first liquid, $\rho_{liquid2}$ is a density of a second liquid in the mixture, and $\rho_G$ is a density of the gas.

14. The apparatus of claim 13, wherein the first device includes at least one of a Coriolis meter and a gamma densitometer.

15. The apparatus of claim 1, wherein the parameter sensed by the first device includes an amount of microwave energy absorbed by the mixture, and the signal processor determines the fluid cut using the equation:

$$\Phi_{compensated} = \Phi_{liquid\ 1} - \Phi_G$$

where: $\Phi_{compensated}$ is the compensated fluid cut of the first liquid, $\Phi_{liquid\ 1}$ is the fluid cut of the first liquid provided by the first device, and $\Phi_G$ is the concentration of the gas.

16. The apparatus of claim 15, wherein the fist device includes a microwave absorption watercut meter.

17. The apparatus of claim 1, wherein the second meter includes at least two strain sensors disposed at different axial locations along the pipe, each of the strain sensors providing a respective strain signal indicative of acoustic pressure disturbances within the pipe at a corresponding axial position.

18. The apparatus of claim 17, wherein the second meter determines the slope of an acoustic ridge in the k-ω plane to determine a speed of sound propagating through the mixture.

19. The apparatus of claim 17, wherein the at least two sensors include 3, 4, 5, 6, 7, 8, 9, 10, 11, 12, 13, 14, 15, or 16 sensors.

20. A method for providing a corrected liquid phase fraction measurement of a first liquid component of a multi-liquid mixture, the multi-liquid mixture flowing through a pipe, and the corrected liquid phase fraction measurement beilng compensated for entrained gas flowing with the multi-liquid mixture through the pipe, the method comprising:
determining an uncorrected liquid fraction of the first liquid component in response to at least one first parameter of the mixture, and providing a first signal indicative of the uncorrected liquid phase fraction;
determining a phase fraction of the gas in the multi-liquid mixture, and providing a second signal indicative of the phase fraction of the gas; and
determining, in response to the first and second signals, the corrected liquid phase fraction measurement which is the uncorrected liquid phase fraction of the first liquid component compensated for the entrained gas.

21. The method of claim 20, wherein the mixture includes oil and water and the first liquid component is selected from one of oil and water.

22. The method of claim 20, wherein the speed of sound propagating through the mixture is determined using at least two strain sensors at different axial locations along the pipe through which the mixture flows, each of the strain sensors providing a respective pressure signal indicative of a pressure disturbance within the pipe at a corresponding axial position, and the speed of sound propagating through the mixture is detennined in response to the pressure signals.

23. The method of claim 20, wherein the at least one parameter determined includes the permittivity of the mixture.

24. The method of claim 20, wherein the determining of the at least one parameter is determined using a microwave fluid cut meter.

25. The method of claim 20, wherein the determining of the at least one parameter is determined using a microwave watercut meter.

26. The method of claim 20, further includes determining a slope of an acoustic ridge in the k-ω plane to determine a speed of sound propagating through the mixture.

27. The method of claim 20, further includes measuring the speed of a one dimensional acoustic wave propagating axially through the mixture.

28. The method of claim 20, further includes determining the phase fraction of a second liquid of the mixture, in response the first and second signals.

29. The method of claim 20, wherein the at least one first parameter includes a density of the mixture, and the compensated fluid cut is determined using the equation:

$$\Phi_{compensated} = \Phi_{liquid\ 1} - \phi_G \frac{\rho_{liquid2} - \rho_G}{\rho_{liquid2} - \rho_{liquid1}}$$

where: $\Phi_{compensated}$ is the compensated fluid cut of the first liquid, $\Phi_{liquid1}$ is the fluid cut of the first liquid, $\Phi_G$ is the concentration of the gas, $\rho_{liquid1}$ is a density of the first liquid, $\rho_{liquid2}$ is a density of a second liquid in the mixture, and $\rho_G$ is a density of the gas.

30. The method of claim 29, wherein the density of the mixture is determined using one of a Coriolis meter and a gamma densitometer.

31. The method of claim 20, wherein the multi-liquid mixture includes at least a second fluid component, the at least one first parameter includes a permittivity of the mixture, and the corrected liquid phase fraction measurement of the first liquid component is determined using the equation:

$$\Phi_{compensated} = \Phi_{liquid\ 1} - \phi_G \frac{\sqrt{\varepsilon_{liquid2}} - \sqrt{\varepsilon_G}}{\sqrt{\varepsilon_{liquid2}} - \sqrt{\varepsilon_{liquid1}}}$$

where: $\Phi_{compensated}$ is the corrected liquid phase fraction measurement of the first liquid component, $\Phi_{liquid\ 1}$ is the uncorrected liquid phase fraction of the first liquid component, $\Phi_G$ is the phase fraction of the gas, $\varepsilon_{liquid1}$ is a permittivity of the first liquid component, $\varepsilon_{liquid2}$ is a permittivity of the at least second liquid component, and $\varepsilon_G$ is a permnittivity of the gas.

32. The method of claim 31, wherein the permittivity of the mixture is determined using a resonant microwave oscillator.

33. The method of claim 20, wherein the at least one first parameter includes an amount of microwave energy absorbed by the mixture, and the fluid cut is determined using the equation:

$$\Phi_{compensated} = \Phi_{liquid\ 1} - \Phi_G$$

where: $\Phi_{compensated}$ is the compensated fluid cut of the first liquid, $\Phi_{liquid\ 1}$ is the fluid cut of the first liquid, and $\Phi_G$ is the concentration of the gas.

34. The method of claim 33, wherein the amount of microwave energy absorbed by the mixture is determined using a microwave absorption watercut meter.

35. The a method of claim 20, wherein determining the phase fraction of the gas includes using a second meter including at least two strain sensors disposed at different axial locations along the pipe, each of the strain sensors providing a respective strain signal indicative of acoustic pressure disturbances within the pipe at a corresponding axial position.

36. The method of claim 35, wherein the at least two sensors include 3, 4, 5, 6, 7, 8, 9, 10, 11, 12, 13, 14, 15, or 16 sensors.

* * * * *